US00RE46049E

(19) United States
(12) Reissued Patent
Lipson et al.

(10) Patent Number: US RE46,049 E
(45) Date of Reissued Patent: Jul. 5, 2016

(54) AUTOMATIC EXTERNAL DEFIBRILLATOR FOR THE DIAGNOSIS OF STROKE

(75) Inventors: David Lipson, Ithaca, NY (US); Peter Forrest, Inver Grove Heights, MN (US)

(73) Assignee: Koninklijke Philips Electronics N.V., Eindhoven (NL)

(21) Appl. No.: 13/204,984

(22) Filed: Aug. 8, 2011

Related U.S. Patent Documents

Reissue of:
(64) Patent No.: 7,037,267
Issued: May 2, 2006
Appl. No.: 09/711,440
Filed: Nov. 13, 2000

U.S. Applications:
(62) Division of application No. 11/823,811, filed on Jun. 27, 2007, now Pat. No. Re. 42,803, which is an application for the reissue of Pat. No. 7,037,267.

(60) Provisional application No. 60/164,586, filed on Nov. 10, 1999.

(51) Int. Cl.

| | |
|---|---|
| ***A61B 8/02*** | (2006.01) |
| ***A61B 8/06*** | (2006.01) |
| ***A61B 8/08*** | (2006.01) |
| ***A61B 5/00*** | (2006.01) |
| ***A61B 8/00*** | (2006.01) |
| *A61B 8/14* | (2006.01) |
| *A61B 5/026* | (2006.01) |
| *A61B 6/00* | (2006.01) |
| *G01S 7/52* | (2006.01) |

(Continued)

(52) U.S. Cl.
CPC ..... *A61B 8/0808* (2013.01); *A61B 5/6834* (2013.01); *A61B 8/06* (2013.01); *A61B 8/4281* (2013.01); *A61B 8/4416* (2013.01); *A61B 5/026* (2013.01); *A61B 5/02438* (2013.01); *A61B 6/501* (2013.01); *A61B 6/5247* (2013.01); *A61B 8/481* (2013.01); *A61N 7/00* (2013.01); *G01S 7/52036* (2013.01); *Y10S 128/92* (2013.01)

(58) Field of Classification Search
CPC ..... A61B 8/0808; A61B 8/06; A61B 8/4281; A61B 8/4416; A61B 8/481; A61B 5/6834; A61B 5/02438; A61B 5/026; A61B 6/501; A61B 6/5247; A61N 7/00; G01S 7/52036; Y01S 128/92
USPC ..... 600/437, 451, 454, 465, 468
See application file for complete search history.

(56) References Cited

U.S. PATENT DOCUMENTS 3,948,248 A * 4/1976 Zuckerman et al. ..... 600/457
4,237,901 A * 12/1980 Taenzer ..... 600/443

(Continued)

OTHER PUBLICATIONS

Alexandrov, A.V., et al., "Transcranial Doppler; An Overview of its Clinical Applications," Journal of Emergency and Intensive Care Medicine, 2000, vol. 4, No. 1. pp.

(Continued)

*Primary Examiner* — Long V Le
*Assistant Examiner* — Angela M Hoffa

(57) ABSTRACT

A medical diagnostic method, system and related equipment particularly adapted to diagnose disorders of the blood circulation serving the head and neck, and especially the brain. A preferred use of the system is early, rapid, accurate, diagnosis of stroke, especially whether the stroke is due to blockage of a blood vessel or leakage from the blood vessel.

16 Claims, 6 Drawing Sheets

Amended

(51) Int. Cl.
*A61N 7/00* (2006.01)
*A61B 5/024* (2006.01)

(56) References Cited

U.S. PATENT DOCUMENTS

| | | | | | |
|---|---|---|---|---|---|
| 4,575,799 | A | | 3/1986 | Miwa et al. | |
| 4,692,139 | A | | 9/1987 | Stiles | |
| 4,951,653 | A | | 8/1990 | Fry et al. | |
| 5,058,592 | A | | 10/1991 | Whisler | |
| 5,188,106 | A | * | 2/1993 | Nappholz et al. | 607/24 |
| 5,247,938 | A | * | 9/1993 | Silverstein et al. | 600/459 |
| 5,379,770 | A | | 1/1995 | Van Veen | |
| 5,388,583 | A | * | 2/1995 | Ragauskas et al. | 600/451 |
| 5,409,005 | A | | 4/1995 | Bissonnette et al. | |
| 5,471,988 | A | | 12/1995 | Fujio et al. | |
| 5,477,858 | A | | 12/1995 | Norris et al. | |
| 5,503,152 | A | | 4/1996 | Oakley et al. | |
| 5,509,896 | A | | 4/1996 | Carter | |
| 5,690,117 | A | * | 11/1997 | Gilbert | 600/463 |
| 5,695,460 | A | | 12/1997 | Siegel et al. | |
| 5,919,144 | A | | 7/1999 | Bridger et al. | |
| 5,951,477 | A | * | 9/1999 | Ragauskas et al. | 600/438 |
| 6,019,724 | A | * | 2/2000 | Gronningsaeter et al. | 600/439 |
| 6,021,349 | A | * | 2/2000 | Arand et al. | 607/5 |
| 6,027,460 | A | * | 2/2000 | Shturman | 600/585 |
| 6,066,097 | A | | 5/2000 | Glenn et al. | |
| 6,196,972 | B1 | | 3/2001 | Moehring | |
| 6,197,345 | B1 | | 3/2001 | Porter | |
| 6,328,694 | B1 | * | 12/2001 | Michaeli | 600/438 |
| 6,390,982 | B1 | | 5/2002 | Bova et al. | |
| 6,398,772 | B1 | | 6/2002 | Bond et al. | |
| 6,454,757 | B1 | | 9/2002 | Nita et al. | |
| 6,464,680 | B1 | * | 10/2002 | Brisken et al. | 604/501 |
| 6,468,219 | B1 | | 10/2002 | Njemanze | |
| 6,682,483 | B1 | | 1/2004 | Abend et al. | |
| 6,682,502 | B2 | | 1/2004 | Bond et al. | |
| 6,731,981 | B1 | * | 5/2004 | Hemmingsson et al. | 607/13 |
| 6,733,451 | B2 | | 5/2004 | Rabiner et al. | |
| 6,929,632 | B2 | | 8/2005 | Nita et al. | |
| 6,945,937 | B2 | | 9/2005 | Culp et al. | |
| 6,985,771 | B2 | | 1/2006 | Fischell et al. | |
| RE42,803 | E | * | 10/2011 | Lipson et al. | 600/454 |
| 2002/0198469 | A1 | | 12/2002 | Bridger et al. | |

OTHER PUBLICATIONS

Luo, H., et al., "Thrombolysis: Transcutaneous Ultrasound Augments Lysis of Arterial Thrombi in Vivo," Circulation, vol. 94(4), Aug. 15, 1996, pp. 775-778.

Alexandrov, A., et al., "High-Rate of Complete Recanalization and Dramatic Clinical Recovery During fPA Infusion When Continuously Monitored With 2-MHz Transcranial Doppler Monitoring," Stroke, 2000; 31;610-614; downloaded from stroke.ahajournals.org on Jun. 2007.

Olsson, S.B., et al., "enhancement of Thrombolysis by Ultrasound," Ultrsound in Med. & Biol., vol. 20, No. 4, pp. 375-382, 1994.

Akiyama, M. et al., "Low-Frequency Ultrasound Penetrates the Cranium and Enhances Thrombolysis in Vitro" Neurosurgery, vol. 43. No. 4, Oct. 1998, pp. 828-833/.

Seidel, G., et al., "Harmonic Grey Scale Imaging of the Human Brain," Journal of Neuroimaging, vol. 9, 3, Jul. 1999, pp. 171-174.

Nabavi, D., et al., "Diagnostic Benefit of Echocontrast Enhancement for the Insufficient Transtemporal Bone Window," Journal of Neuroimaging, vol., 9, No. 2, Apr. 1999, pp. 102-107.

Ries, F., "Clincal Experience with Echo-Enhanced Transcranial Doppler and Duplex Imaging," Journal of Nueroimaging, Suppl. 1, to vol. 7., Apr. 1997, pp. S15-S21.

Becker, G., et al., "Transcranial Color-Coded Real-Time Sonography of Intracranial Veins," Journal of Neuroimaging vol. 5, No. 2, Apr. 1995, pp. 87-94.

Martin, P.J. et al., "Color-Coded Ultrasound Diagnosis of Vascular Occlusion in Acute Ischemic Stroke," Journal of Neuroimaging, vol. 5, No. 3, Jul. 1995, pp. 152-156/.

Abstracts, Journal of Neuroimaging, 1997, vol. 7, pp. 229-230.

Andrei V. Alexandrov and Matthew Joseph, Transcranial Doppler: An Overview of its Clinical Applications, Journal of Emergency and Intensive Care Medicine, 2000, vol. 4, No. 1.*

* cited by examiner

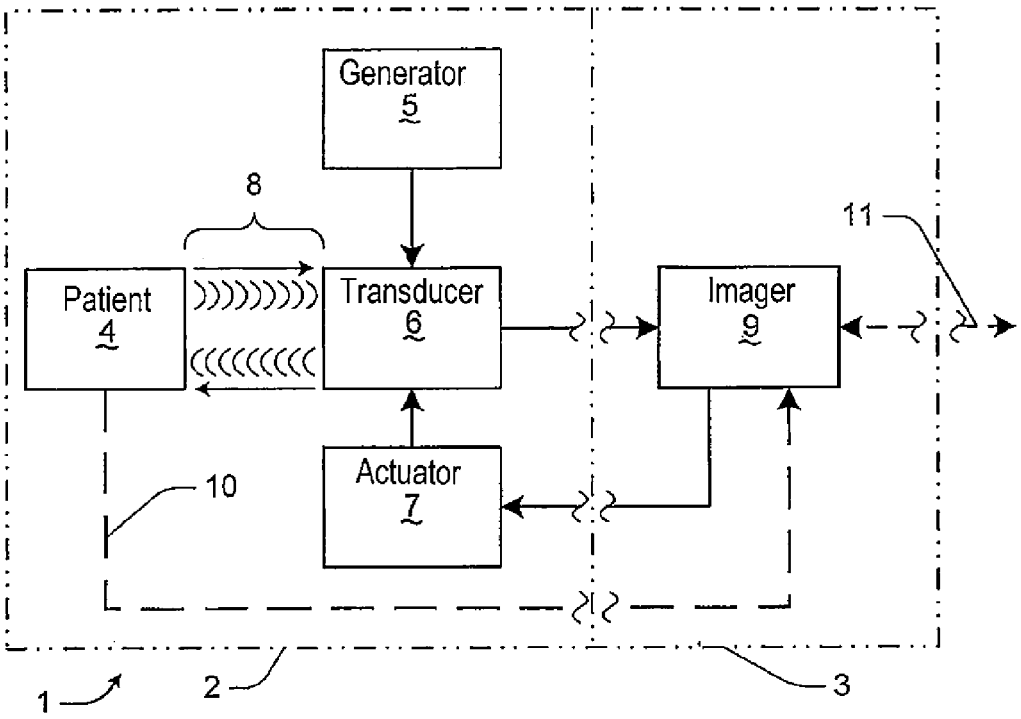
Figure 1 - Amended
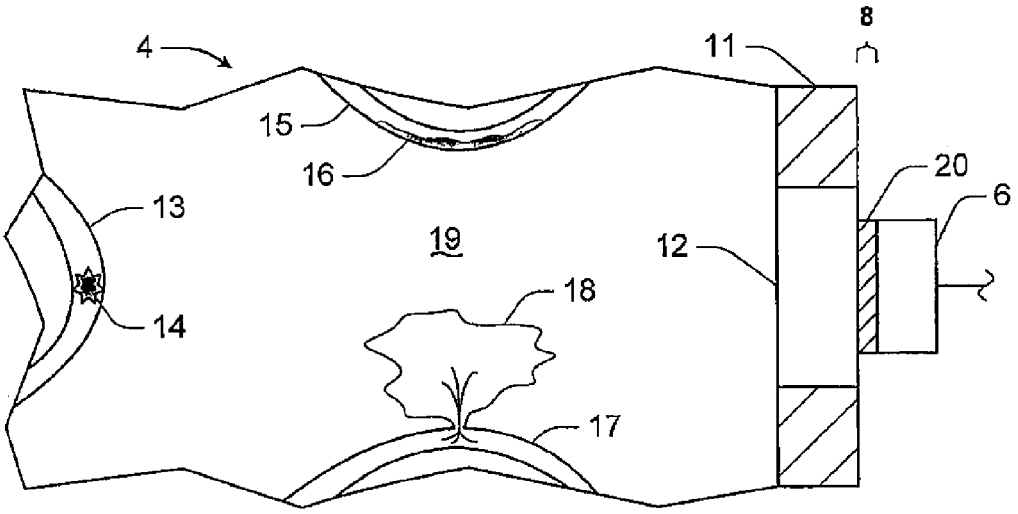
Figure 2

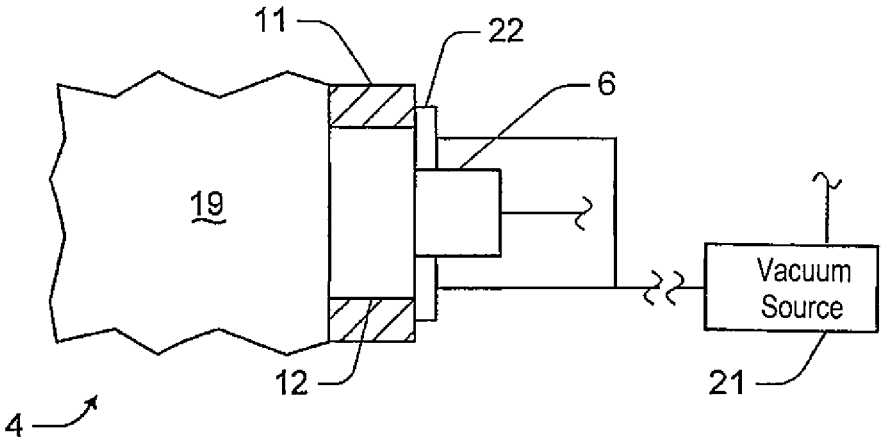
Figure 3 - Amended
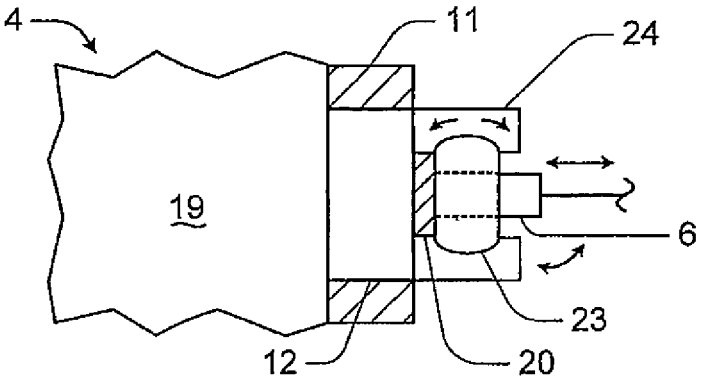
Figure 4

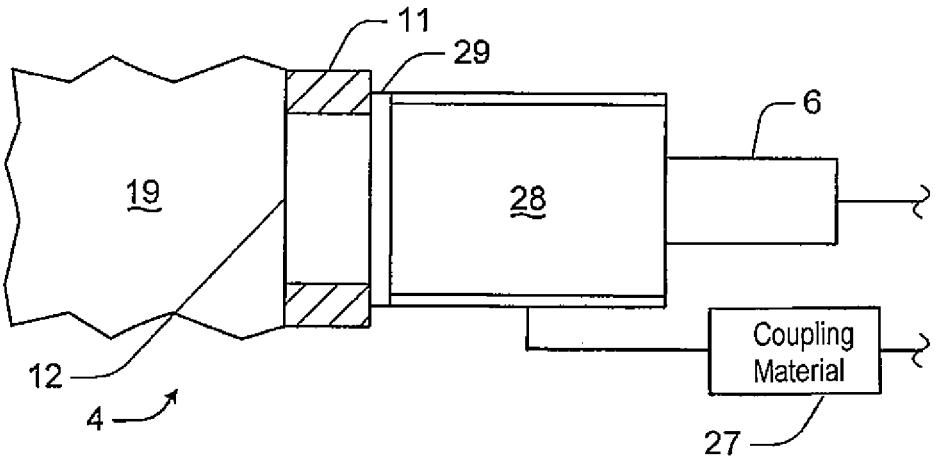
Figure 8 - Amended
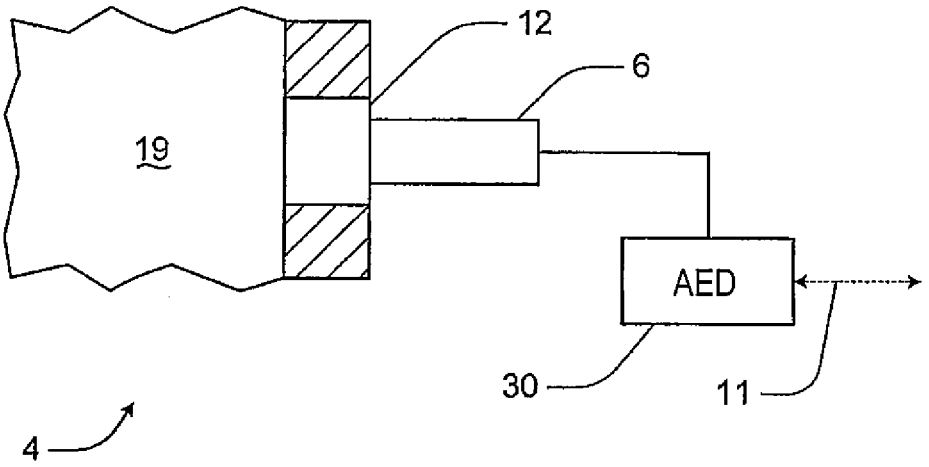
Figure 9 - Amended

AUTOMATIC EXTERNAL DEFIBRILLATOR FOR THE DIAGNOSIS OF STROKE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

*Notice: More than one reissue application has been filed for the reissue of U.S. Pat. No. 7,037,267. This divisional reissue application Ser. No. 13/204,984, claims priority under 35 U.S.C. §120 to reissue application Ser. No. 11/823,811, filed Jun. 27, 2007, which is a reissue of U.S. Pat. No. 7,037,267, filed Nov. 13, 2000, which claims the benefit of U.S. Provisional Application No. 60/164,586, filed Nov. 10, 1999.*

TECHNICAL FIELD

This invention involves medical diagnostic methods, systems, and apparatus, particularly those intended for diagnosis of disorders in the blood supply to the brain.

BACKGROUND

There are many highly accurate techniques for diagnosing disorders of the brain and nervous system. Unfortunately, many of them require large and immovable equipment, extremely sophisticated computers, and highly trained personnel to operate them. They are not suitable for first responders, paramedics and other field medical personnel. They also are not suitable for the rapid use that medical emergencies require. Similarly, they often are not suitable for use in surgical suites where working room is at a premium, and the large electromagnetic fields generated by some types of equipment are not compatible with other equipment, tools, and personnel typically present.

Glossary

This document uses a variety of terms from science, engineering, and medicine. Those not specifically defined below have the meanings that they ordinarily have in those fields. The following is a list of specialized terms most commonly used in this document.

Acoustic window (sometimes, acoustic bone window) refers to a portion of the skull that is thin enough to pass ultrasonic waves.

Aneurysms are portions of blood vessels that bulge outward or break open.

Aural refers to the ear or the hearing (auditor) system.

Cerebral, from the medical term cerebellum, refers to the brain.

Cranium is the medical term for the skeleton of the head, also commonly known as the skull.

Clinicians are people trained in medicine, such as physicians, nurses, paramedics, medical technicians, and the like.

Coupling is causing two or more things to work together.

Diagnosis is the act of determining whether a stroke has occurred, and if so what type it is or is not. It includes the process of "differential" diagnosing, which is identifying one type of stroke simultaneously with ruling out the possibility of another type.

Doppler refers to a technique of analyzing waves, in which the change in time of the frequency of waves reflected from an object indicates the speed at which the object is moving toward or from the observer. It is responsible for the familiar effect that the pitch of a sound rises as the object approaches the observer and lowers as the object goes away from the observer.

Emboli are little particles carried by the bloodstream into smaller blood vessels, where they block blood flow to cells beyond. They can be blood clots, bubbles or solids such as plaque. Emboli is the plural of embolus. Embolic refers to a stroke that is caused by an embolus or emboli. Emboli that lodge in place can cause additional thrombi (see below) to form at the same location.

Harmonic refers to a wave having a frequency value that is a multiple of the frequency of some basic wave, called the fundamental (and usually the wave that is directed to an object). Every complicated wave is mathematically equivalent to a collection of the fundamental wave and all the possible harmonic waves, in varying amounts and intensities.

Hemorrhagic, meaning bloody, refers to bleeding. A hemorrhagic stroke is one due to a leakage of the blood supply serving a portion of the brain.

Hertz, abbreviated Hz, is the unit of frequency of a wave, defined as one complete cycle per second.

Imaging is the use of information about an object to determine, by human eye or by a computer, something about the location or condition of the object. It does not require the creation of an actual display of the image that can be seen by a human, because computers (and really smart people) are fully capable of interpreting the various aspects of an image, such as intensity, location, size, etc., as if they were actually viewing a traditional image. An image can be two- or three-dimensional. An image can be fixed in time (sometimes called a static image), like a photograph, or it can be moving in time (sometimes called a dynamic image), like a motion picture.

Ischemic ("without chemicals") refers to a condition in which tissue does not receive adequate blood supply. An ischemic stroke is caused by a partial or total blockage of the blood supply serving a portion of the brain.

Kilohertz, abbreviated kHz, is a unit of one thousand Hertz.

Microparticulates are very small particles, including microbubbles ("tiny bubbles"), emboli, plaque, and the like.

Nasal refers to the nose.

Neurological refers to the brain and nervous system (the spinal cord and all the nerves).

Nidus is a Latin word for the location of origin of a disease process, such as the point where a blood clot first forms even if the clot travels elsewhere before doing damage.

Ocular refers to the eye.

Opening, in the context of a location of a transducer adjacent the skull, includes a natural opening in the skull, a man-made opening in the skull, or an acoustic window through the bones of the skull.

Orbit is the medical term for the eye socket and the bones of the skull that form it.

Patent is a term used in this document to include not just a cited patent itself, but also any other patent issuing from a patent application claiming priority from the cited patent, e.g., a continuation patent, a continuation-in-part patent, a division (sometimes called a divisional) patent, a reissued patent, or an reexamined patent.

PCT is an acronym for the Patent Cooperation Treaty administered by the WIPO (see below).

Perfusion is a medical term for fluid flow over or through an organ, such as the flow of blood through the cerebral vasculature.

Plaque is the term for fatty deposits that build up on the inside of arteries, sometimes breaking loose and flowing through the body.

Stroke is the term for sudden loss of normal blood flow in a portion of the brain.

Temporary ischemic attacks, or TIAs, are temporary blockages of blood flow in the brain that do not last more than 24 hours. They usually do not last more than a few hours. They generally do not cause permanent damage that is easily perceived by the sufferer or observable by others.

Thrombolytic refers to the process of dissolving a thrombus, or the ability to do so.

Thrombi are a kind of early-stage blood clot. The singular of thrombi is thrombus.

Thrombotic refers to a stroke caused when an artery of the brain narrows to a point at which blood begins to clot at the point of narrowing.

tPA (sometimes t-PA) is the abbreviation for tissue plasminogen activator, a "clot busting" drug known to be effective against ischemic strokes.

Transcranial Doppler, or TCD, is a technique for directing ultrasonic waves through the bones of the skull and analyzing the echoes with [Dopper] *Doppler* techniques.

Transducers are devices that transform one form of energy into another, such as transforming electrical power into ultrasonic waves or vice versa.

Transorbital refers to crossing through the eye socket.

Ultrasound refers to sound waves having frequencies above the range of human hearing, about 20 kHz, depending on the listener's age and previous experience with loud sounds.

Vasculature is the medical term for blood vessels. It includes the arteries that supply fresh blood to tissue, and the veins that carry spent blood away from tissue.

WIPO is an acronym for the World Intellectual Property Organization, an agency of the United Nations that administers an international system for patent applications under the PCT (see above).

DISCLOSURE OF THE INVENTION

The invention represents an entirely new approach to medical diagnostic systems, particularly those used to diagnose stroke. Because of this new approach, the invention can be described in a large number of "embodiments," none more preferred than any other in terms of scope or importance.

Some embodiments of the invention can be described as a method, i.e., a "recipe" or procedure to achieve a result. Others can be described as a system (i.e., a fully operating machine), some as an assembly (ie., a "kit" or collection that is intended to put together in a particular manner, and which may or may not have been put together yet), and yet others as a combination (i.e., a group of parts or pieces that are capable of operation together, even if some were parts already present and others had to be supplied). Similarly, parts or portions of each of these embodiments can be described as subsystems, submethods, subassemblies, or subcombinations.

In all embodiments, the invention involves diagnosis of stroke in a patient. More specifically, the invention permits diagnosis of whether a stroke has occurred, and if so, what type of stroke it is.

The two most common types of stroke are hemorrhagic and ischemic. One way to determine hemorrhagic stroke is to identify at least one region of relatively diffuse blood flow within the patient's brain, i.e., finding a region in which the blood flow is outside the arteries, spreading between the brain cells. One way to determine ischemic stroke is to identify at least one location of inadequate blood flow within the patient's brain. In this sense, "inadequate" flow is any condition in which causes less blood to flow for any reason, such as when one or more arteries serving the brain have a partial or total, are narrowed or otherwise reduced in size. The blood vessel itself may change shape, or it may be blocked or narrowed.

Other embodiments of the invention use a more sophisticated approach and specifically distinguish between hemorrhagic and ischemic strokes. One way to do this is to identify either type of stroke in any manner that positively rules out the other. One particular way to do this is to form a two-dimensional or there-dimensional image of the brain. Such images (either of which could be fixed in time like a snapshot or moving like a motion picture) can be analyzed by a computer or by a clinician to diagnose not just whether the patient has suffered a stroke, but specifically which kind.

Some embodiments use optional additional techniques to enhance stroke diagnosis. For example, Doppler techniques can be used to form an image of the flow of microparticulates. Hemorrhagic stroke can be identified (and the difference between hemorrhagic and ischemic stroke can be identified) based on the relative flow rates of the microparticulates. In another example, harmonic techniques are used to compare the diffusion (if any) of blood How between two or more areas of the brain. As noted before, diffuse blood flow indicates that blood is spreading between cells instead of passing normally through the arteries in the vicinity.

In all embodiments, ultrasonic signals are generated and directed into the brain. The ultrasonic waves strike their target, namely the brain tissue, the blood vessels, and the blood itself. Some of the ultrasonic energy is reflected, forming a reflected signal, or echo, from the brain. Different targets produce different echoes. The echoes are received and processed into information that indicates the identity of the target, that is, the condition of the patient's brain.

Information from at least one reflected ultrasonic signal is analyzed to diagnose the patient. This may be accomplished using any convenient method or equipment already known to those skilled in the art of medical ultrasonic diagnosis. In general, the signals are converted into digital data and analyzed by a computer. Either the computer program will diagnose the presence and type of stroke, or it will present the data in any convenient manner so that a clinician may make the diagnosis. For example, the program may produce the two-dimensional or three-dimensional images described earlier.

A single ultrasonic transmitter, or several such transmitters, may be used to generate the ultrasonic signals. A single ultrasonic receiver, or several such receivers, may be used to detect the ultrasonic echoes. It is typical, but not required, for an ultrasonic transmitter and receiver to be combined into a single unit. Therefore, the remainder of this document uses the term transmitter/receiver with the understanding that the term includes a transmitter only, a receiver only, or both a transmitter and a receiver together. In the case of a transducer and receiver together, the term includes physical or functional combinations, or separate devices that operate together as if they were physically or functionally combined.

There may be one or more transmitter/receiver. Each may perform independently of the other, such as the case where one serves as the backup to the other. However, if independent transmitter/receivers disagree as to the presence, location, or extent of a stroke, it is necessary to ignore one of them (for whatever reason, such as additional data gathered from another source), or to employ some other technique for resolving the disagreement. For example, one could require that they agree with each other, either completely or within some "confidence level" or other way of designating agreement, otherwise a stroke is not detected.

In a more advanced design, the signals from multiple transmitter/receivers may be coordinated together to provide a more robust diagnosis. For example, the image areas of two transmitter/receivers can be arranged to overlap and form a larger image area than either could provide alone. (The overlapping coverage of two automotive headlights is a common analogy.) This may lead to a situation in which "disagreement" between transmitter/receivers is expected. For example, a first transmitter/receiver may detect a stroke in an area outside the view of a second transmitter/receiver. The second unit should not also indicate a stroke (a so-called "false positive") unless it is detecting a separate location of damage to the brain. However, if the first transmitter/receiver detects a stroke within the common area, and the second transmitter/receiver does not indicate a stroke, some other way to resolve the conflict must be used, as indicated before.

Each transmitter/receiver can be placed in any number of locations on the patient's head, including (a) natural openings in the skull, (b) man-made openings in the skull; and (c) known acoustic windows in the skull (some of which are also natural openings but some of which are regions where the skull is relatively thin but not open naturally).

In the case of a transmitter/receiver that is mounted adjacent a natural opening in the patient's skull, the typical locations are the ocular openings (i.e., the eye sockets or orbits), the nasal openings, and the aural openings. Manmade openings can be made in any convenient location using techniques known to neurosurgeons such as drilling a hole, removing a plate-shaped portion of skull, etc. It is optionally possible to use equipment designed to attach to the skull and provide a support for instruments. For example, the fixed base and movable/lockable ball-and-socket approach disclosed in International Publication Number WO 98/51229 (International Patent Application Number PCT/US98/51229) could be modified to accommodate a transducer/receiver instead of catheters.

Known acoustic windows include those known to clinicians as the anterior temporal window, the posterior temporal window, the middle temporal window, the transorbital window, the lateral frontal window, the paramedian frontal window, and the suboccipital foramen magnum window.

Ultrasonic systems produce or detect signals better if a transmitter/receiver is "acoustically coupled" in the vicinity of the natural or man-made opening, thus reducing signal loss due to reflection and dissipation when the ultrasonic waves strike (from either direction) the surface of the tissue immediately within the opening. Often it is sufficient for the transmitter/receiver to fit tightly within the opening and physically contact the tissue surface (or the surface of other tissue which itself is acoustically coupled to the tissue of interest).

The apparatus may improve the acoustic coupling if a tight fit is not present. This includes any way of moving or pushing the transmitter/receiver into greater contact with the opening, or with the tissue itself, or both. For example, a vacuum subsystem could be used to pull the transmitter/receiver toward the opening or the tissue. Or, a motor and linkage could be used to push the transducer/receiver toward the opening or the tissue. Or, an electronic or software-based correction could be made as part of the imaging process. Of course, combinations of any two or more of these examples (or other approaches) could be used.

In other embodiments, to improve the quality of the acoustic coupling (and maintain sterile conditions), an optional "acoustic coupling material" may be located between the transmitter/receiver and either the opening, the tissue, or both. Several such materials are already known, such as mineral oil, glycerin, propylene glycol, water and water-based gels. Acoustic coupling material may be used alone or together with any suitable subsystem to improve acoustic coupling.

In an even more specific arrangement, the actual degree or quality of the acoustic coupling is determined, and the image of the brain is modified to account for that determination. This could involve, for example, basing the determination of to the type of stroke, in part, on the degree or quality of the acoustic coupling. In the specific case in which an acoustic coupling material is used, the degree or quality of the acoustic coupling could be taken to be the same as, or in some manner related to, the amount of acoustic coupling material present.

There are several embodiments of the invention that differ only in the manner in which the acoustic coupling material is used. The acoustic coupling material can be inserted into or removed from the apparatus. For example, a hole or other opening may allow the material to be inserted into its proper location. The positioning of the material could be done manually, or automatically by dispensing the acoustic coupling material into position between the ultrasonic transmitter/receiver and the opening in the skull. Optionally, the acoustic coupling material may be within (or otherwise supported by) a disposable piece that can be either manually or automatically inserted into or removed from the apparatus. Other embodiments would also include those in which the acoustic coupling material is received into position between the ultrasonic transmitter/receiver and the opening in the skull. The apparatus could have some type of feature to ensure that the disposable piece containing the acoustic coupling material fits into the apparatus only in a certain position or orientation. In another example, the apparatus, the disposable piece, or both could have features to ensure that the disposable piece containing the acoustic coupling material is used only once.

A variation on this theme involves preventing the proper operation of the invention unless a sufficient degree or quality of acoustic coupling is present. For example, either the invention is "locked out" because it detects that acoustic coupling is not present, or the apparatus is locked out unless some minimum sufficient amount of coupling is present. (Again, these conditions of acoustic coupling could be correlated with the actual quantity of acoustic coupling material, if such material is used.) One way of locking out the apparatus is to prevent imaging in the absence of sufficient acoustic coupling. Another way of accomplishing the same result is for the apparatus to enable imaging only in the presence of sufficient acoustic coupling. Any form of mechanical, electrical chemical, software-based, or other lockout technique is suitable.

A higher level of complexity is "closed loop" control of the degree or quality of the acoustic coupling (which could be the control of the amount of acoustic coupling material) based on image quality. That is, if the apparatus detects a degree of acoustic coupling that is near the adequate amount, the apparatus adjusts itself to improve the acoustic coupling. This could, for example, mean automatically increasing the amount of vacuum, or increasing the amount of acoustic coupling material by transferring the proper amount from some reservoir within (or adjacent to but under the control of) the apparatus.

In any embodiment, the transmitter/receiver should be held in its acoustically coupled position while transmitting or receiving ultrasonic waves. Because this is not always possible, the various embodiments of the invention use the technique of "dynamic coupling" to maintain or improve the ability of the invention to diagnose stroke in real time.

For example, dynamic coupling could be done by permitting the transmitter/receiver to move, but automatically detecting the amount and direction of such motion (in any convenient manner) and using such information for either of two purposes (or for some combination of the two). In either purpose, the motion of the transmitter/receiver does not reduce the ability to diagnose stroke; in fact, it may improve that ability.

The first purpose is to simply move the transmitter/receiver back to its original location, a subprocess known as "stabilization" for purposes of this invention. This subprocess is passive in the sense that it assumes that returning the transducer/receiver back to its former position is all that is needed under the circumstances.

The second purpose is to compensate for changes in the ultrasonic signal (either the transmitter signal or the echoed signal), if any, caused by the motion. This second purpose may involve actually moving the transducer/receiver, or it may involve modification of the imaging process, or some combination of the two. The second purpose is accomplished in a subprocess known as "compensation" for purposes of this invention. This subprocess is active in the sense that the quality of diagnosis determines the extent of motion of the transducer/receiver, or the type or amount of image modification, or both.

The vacuum system described above in the context of acoustic coupling is one preferred component of the dynamic coupling subsystem. In one embodiment, a platform defining one or more suction ports is positioned adjacent the opening in the skull. The platform is held to the patient by applying suction to at least one suction port. The ultrasonic transmitter/receiver is supported by the platform. Thus, by dynamically controlling the amount and location (in the case of multiple independent suction ports) of the vacuum, the transmitter/receiver is dynamically stabilized. Preferred configurations of this embodiment are suitable for curved, oval or circular openings: the platform forms a curved, oval, or circular arc so that the platform surrounds at least a portion of the opening. Even more preferred is a platform having at least two portions, each of which is shaped in at least a portion of the curve, oval, or circle, and arranged on generally opposite sides of the opening. Even more portions are possible, and such multi-portion embodiments permit greater control over the dynamic coupling technique.

Instead of a vacuum-based subsystem (or working together with it), actuators of any suitable type may be used to either improve the acoustic coupling, or to move the transmitter/receiver.

Another technique of dynamic coupling combines multiple diagnostic techniques for purposes of improving the overall value of the diagnosis. For example, any embodiment described above that employs ultrasonic imaging may be combined with any other technique for diagnosis of stroke. Data from the non-ultrasound technique can then be used to modify the image from the ultrasound transducer/receiver, or the diagnosis based on that image. Similarly, an overall diagnosis may be made using any combination of individual results from each technique. Suitable non-ultrasonic diagnostic methods include, but are not limited to: computed tomography ("CT") scanning; magnetic resonance ("MR") scanning; differential spectrophotometric methods, near-infrared detection of tissue characteristics; detection or measurement of certain biological materials or chemicals (e.g., the enzyme known as S100β), which could be done by any convenient method, including use of miniature silicon electronic biological assays ("lab-on-a-chip") and techniques; detection of changes such as blood pressure, pressure within the eye, blood flow in the arteries serving organs other than the brain (such as those serving the eye), etc. For convenience, the apparatus used in a non-ultrasonic diagnostic technique is also referred to as a transducer/receiver below, because functions analogous to those of an ultrasonic transducer/receiver are also being performed.

In any embodiment, the invention may be adapted into a portable version suitable for use by first responders, paramedics and other field medical personnel. This involves modifications such as portable power supplies (e.g., single use or rechargeable batteries); or equipping the invention with suitable telemedicine features such as wireless transmission of data, on-board or remote data storage, etc.; or equipping the invention with features such as self-check diagnostics, alphanumeric or graphical displays of menus, commands, or other information, and the like.

Some versions of the invention are combinations of separate transducer units that mount in vacuum coupler units and are connected to image processor units. Others are unified or integrated combinations, such as a helmet-based unit in which the transducer, vacuum units, and image processors are all mounted on the helmet.

In any embodiment, image processing may include the use of expert systems, neural networks, or both.

In any embodiment, the invention may be adapted to for use in surgical suites. For example, the invention may be employed during or after cardiac surgery to detect strokes that are known to occur as complications in a small number of such cases.

In any embodiment, the invention may be employed to additionally deliver ultrasonic energy during the administration of therapy, such as tPA, in response to a diagnosis of stroke, so that the ultrasonic energy may improve the effectiveness of the therapy.

BRIEF DESCRIPTION OF THE DRAWINGS

FIGS. 1-5 are schematic diagrams of various embodiments of the invention.

FIGS. 8-10 are schematic diagrams of other various embodiments of the invention.

Figure 5:
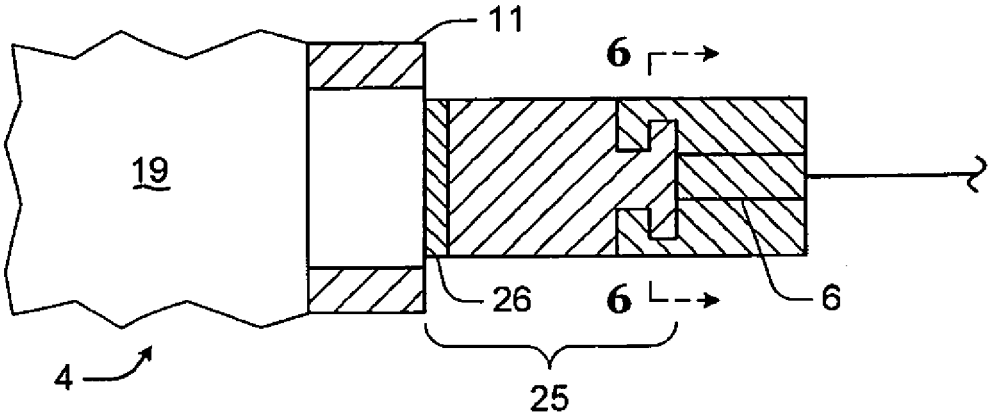

The drawings are schematic representations only. They are not intended to show all specific details discussed below, or those that might be included in a commercial version of any such embodiment. Features shown in one or more Figures could be combined, even if they are not illustrated together in a single FIGURE.

DETAILED DESCRIPTION

The following description is not intended to limit the technological or legal scope of the invention. For example, examples of various embodiments of the invention are only aids to understanding the features, functions, and benefits of the invention in its broadest sense.

FIG. 1 is a schematic diagram of an embodiment of the invention in use, a situation generally indicated as 1. Boxes 2 and 3 illustrate portions of this embodiment that optionally may be physically separated from each other, but act cooperatively, using standard remote communications techniques, whether wired or wireless. The invention is used to diagnose stroke in a patient 4. Ultrasonic energy is generated in generator 5, then sent to and received from the patient 4 by transducer 6. The imager 9 interprets the reflected signal, which is affected (in part) by the nature and quality of the dynamic coupling 8 of the transducer 6 to the patient 4. The scope of the invention is not limited to the manner in which the nature and quality of dynamic coupling 8 is determined. For example, one of many potential techniques is the use of one or more contact sensor(s), pressure sensors, position sensors, etc. (all not shown), according to known principles. Another very important way is analysis of the quality and nature of the reflected ultrasonic signal itself, such as by comparison to baseline data or other parameters.

In any event, actuator 7 may improve the diagnosis in a closed feedback and control loop. In this regard, it should be emphasized that FIG. 1 is schematic only and that the invention is not limited to a separate and/or mechanical actuator 7 operating directly on transducer 6, although that is one possible embodiment. The invention includes electronic "actuation" in the sense of electronic and/or mathematical adjustment to any or all of generator 5, transducer 6, imager 9, or (as described below) dynamic coupling 8 itself.

In general, imager 9 performs any process for identifying data relevant to the diagnosis of stroke. This includes techniques for automatically detecting symptoms based on any relevant criteria. The imaging may be qualitative or quantitative in nature and/or the manner in which it is reported. For example, imager 9 may execute an algorithm for scanning the brain to identify potentially likely symptoms of stroke, then analyze such regions in greater detail using one or more techniques. In doing so, it may perform digital calculations related to the diagnosis of stroke and transmit relevant data to a remote location for full diagnosis and/or confirmation using telemedicine techniques. Yet, in the vicinity of the patient, the result of the calculation may be reported in only a simpler "stroke/no stroke" manner, such as a display which is colored red for adequate perfusion and blue for inadequate perfusion, however quantitative the basis for determining adequacy of perfusion may be.

An optional, non-ultrasonic, detection of symptoms of stroke, illustrated schematically as 10, may also be used confirm, modify, or reject a diagnosis of stroke; as an input to the dynamic coupling of transducer 6 to the patient 4; or as input to the imaging process.

An optional wired or wireless communication link 11 may be used to transmit any form or content of data to another location, for any purpose. This would include any manner of reporting the results of the diagnosis as described above, or any other relevant information about the status of the system, the patient, etc.

FIG. 2 is a schematic representation of another embodiment of the invention. Transducer 6 is dynamically coupled to the patient 4 between transducer 6 and the patient's skull 11 in the vicinity of an opening 12. In the embodiment shown in the Figure, an optional by acoustic material 20 is used to improve the acoustic coupling of transducer 6 to the patient. The relative sizes of the transducer 6, amount of acoustic material 20 (if used), and opening 12 are shown in schematic form only.

Within the patient's brain 19 are several portions of cerebral vasculature that are imaged by the invention to diagnose stroke in the patient 4. Artery 13 is blocked by blockage 14 and thus the flow of blood downstream is inadequate. This is an example of ischemic stroke. Artery 15 is partially blocked by partial blockage 16 and thus the flow of blood downstream is diffused by the partial blockage and may be detected accordingly. (Typical whole or partial blockages are plaque, emboli, and the like.) By contrast, artery 17 is not blocked at all, but it has burst and thus diffuse blood flow 18 is present outside the vasculature and may be detected accordingly. This is an example of hemorrhagic stroke. Of course, these descriptions are for ease of illustration and should not be taken as limitations on the usual and well-understood medical description of the various types of stroke and the mechanisms that cause them. In any event, transducer 6 is used to diagnose any or all of these conditions in the patient in accordance with the principles of the invention.

FIG. 3 is a schematic illustration of an alternative (or additional) dynamic coupling technique. Vacuum source 21 is used to generate and (if desired) control the dynamic coupling of transducer 6 to the patient 4, by use of a vacuum in chamber 22.

FIG. 4 is a schematic illustration of an alternative (or additional) actuation technique. Transducer 6 is mounted so as to move in one, two, or (as illustrated) three directions according to the motion of ball 23 in socket 24. There are many specific techniques and devices for such actuation, and the invention is not limited to any of them, thus they are not shown for clarity.

Figure 6:
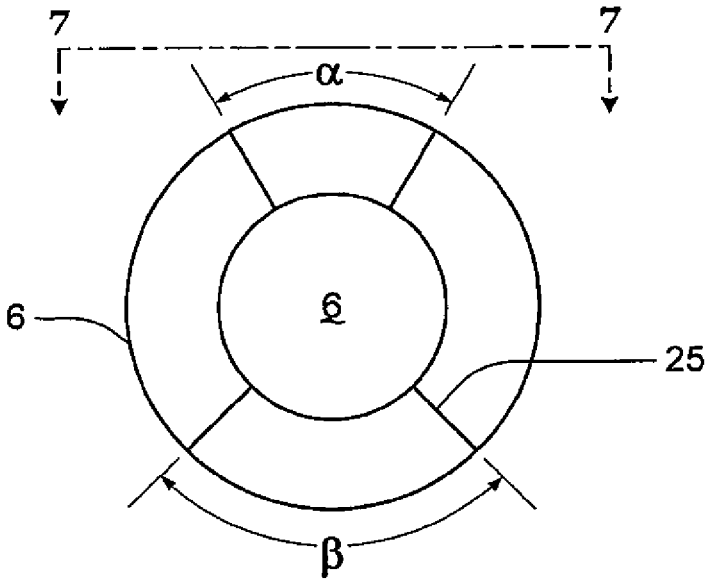
FIG. 6 is a schematic cross sectional diagram taken along line 6-6 of FIG. 5.
Figure 7:
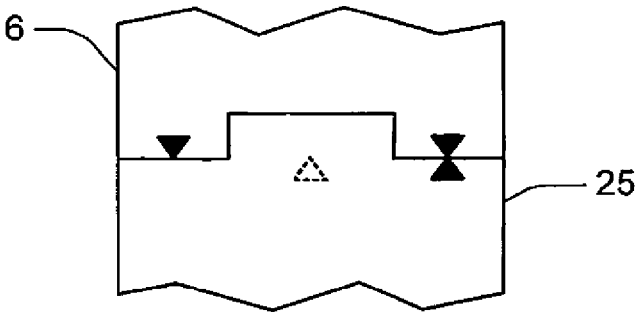
FIG. 7 is a schematic cross sectional diagram taken along line 7-7 of FIG. 6.

FIGS. 5-7 are schematic illustrations of an alternative (or additional) acoustic material application technique. Acoustic material is contained within a separate (reusable or disposable) cartridge 25 that has a removable release liner (not shown for clarity) or an acoustically transparent window or fabric 26 designed to contact patient 4. Cartridge 25 connects to transducer 6 by some appropriate interlock technique. For example, FIG. 6 shows an interlock in which the angles $\alpha$ and $\beta$ are different from each other to ensure that the cartridge is oriented properly. FIG. 7 shows the use of marks to indicate proper rotation of cartridge 25 onto transducer 6. In any or all of these embodiments, cartridge 25 could be connected to an adapter or other intermediate feature instead of directly to transducer 6.

FIG. 8 schematically illustrates an embodiment in which a system for dispensing acoustic coupling material across in a controlled manner is used. A source 27 of acoustic coupling material replenishes a chamber 28 that couples the transducer 6 to the patient 4 through some type of interface 29 (for example, the acoustically transparent window or fabric 26 of FIG. 7). As before, the source 27 can act in the role of the actuator 7 and thus be part of the closed loop control of the dynamic coupling of transducer 6. Chamber 28 may be part of a removable or disposable cartridge 25 as shown in FIGS. 5-7.

FIG. 9 schematically illustrates the combination of the invention as previously described into an otherwise conventional portable automatic external defibrillator (AED) 30. There are many advantages to this combination, including (without limitation) the ability to share a common power supply (batteries, recharging circuits for rechargeable batteries, etc.) and associated switches (e.g., a main power on-off circuit controlled by a switch connected to a lid that opens and closes); common data storage and removal (either by way of telecommunications link 11, conventional removable data storage media, PC cards, etc.); common ambient condition and battery condition temperature sensors; coordinated detection of whether the defibrillator electrode gel and the ultrasonic transducer acoustic coupling material are still suitable for use, based on temperature, age, or other factors;

common audio/visual techniques and equipment for prompting users to follow proper procedures for "one-touch" or other proper use of the equipment, depending on the symptoms observed in the patient and/or instructions received from remote medical personnel (e.g., pre-hospital procedures such as the Los Angeles Prehospital Stroke Screen); common self-test and diagnostic routines (whether performed according to a schedule, periodically, at random times, as dictated by equipment usage, etc.); coordinated remote transmission of the status of such routines over the telecommunications link 11, or a shared communications port; and so on. Even greater advantages lie in the use of the electrocardiogram (ECG or EKG) data gathered by conventional AEDs as input into the dynamic coupling and/or imaging components of the stroke diagnosis. Such data may be used to confirm, modify, or reject a diagnosis, in a manner similar to that described for the non-ultrasonic detection of symptoms of stroke described above. Of course, any of the features just mentioned that do not specifically require presence of an AED could be implemented in a "stand-alone" embodiment of the invention.

FIGS. 10-14 schematically illustrate an embodiment of the invention suitable for the acoustic bone window represented by the eye sockets. In each of these Figures, transducer 6 is shown as a matter of convenience as having a circular cross section, but this is not a limitation on the scope of the invention. The actual shape of transducer 6 would be dictated by normal considerations of anatomy, engineering design, and the like.

Figure 10:
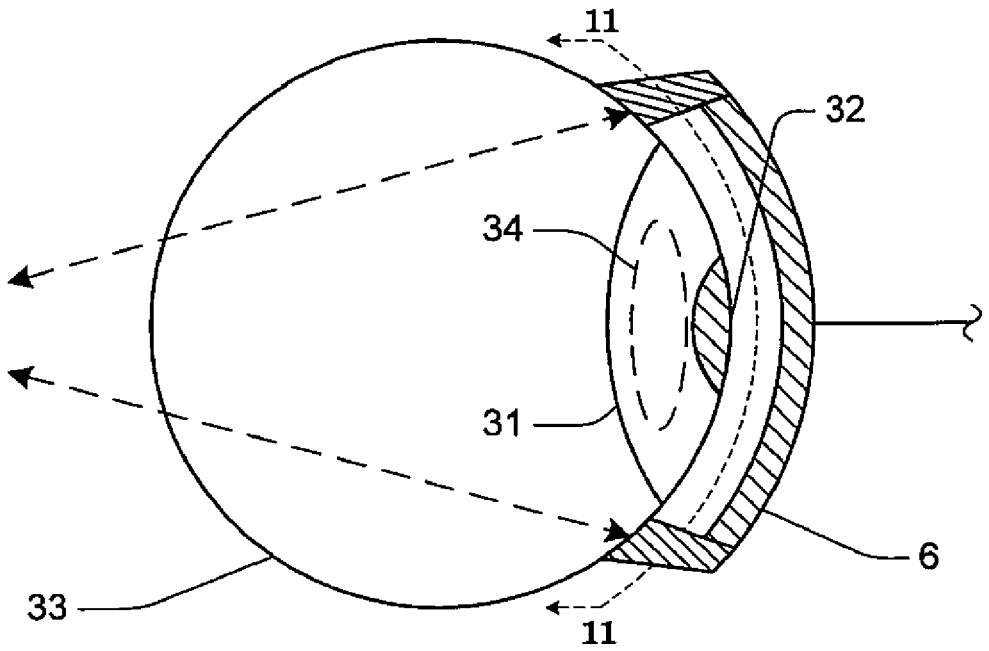
Figure 11:
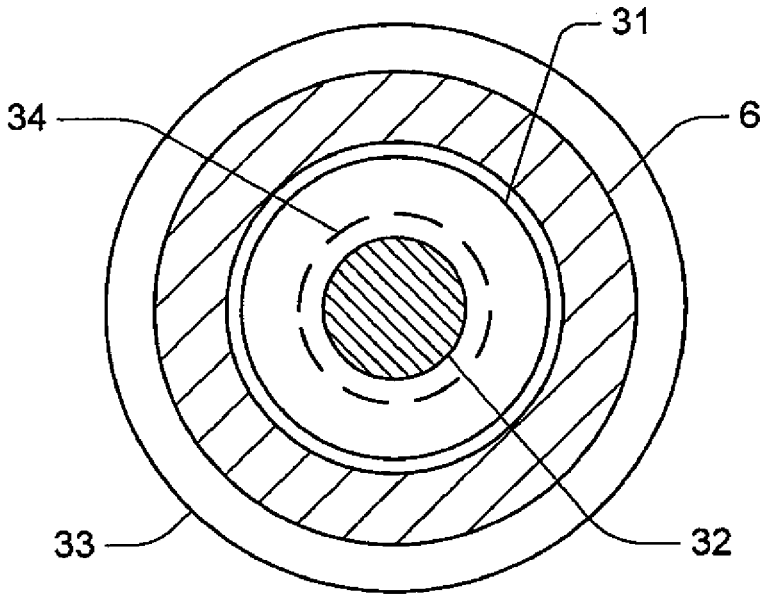
FIG. 11 is a schematic cross sectional diagram taken along line 11-11 of FIG. 10.

FIG. 10 shows an annular transducer 6 arranged to surround the iris 31 (and thus also the pupil 32) of eye 33. For clarity only, these Figures do not show the eyelids, which are transparent at ultrasonic frequencies, but this embodiment would typically be used with the eyelids closed and transducer 6 in contact with them instead of directly with eye 33. As indicated by the dashed arrows, transducer 6 would transmit and receive ultrasonic energy through the eye to the brain of the patient; the annular design reduces the amount of acoustic energy passing through the lens 34 (shown in dashed lines) within the eye 33 so as to minimize adverse effects such as cataracts. Other reductions in energy follow from designing transducer 6 to minimize the amount of acoustic energy that spreads in so-called "side lobes" from the main path of travel indicated in FIG. 10.

Figure 12:
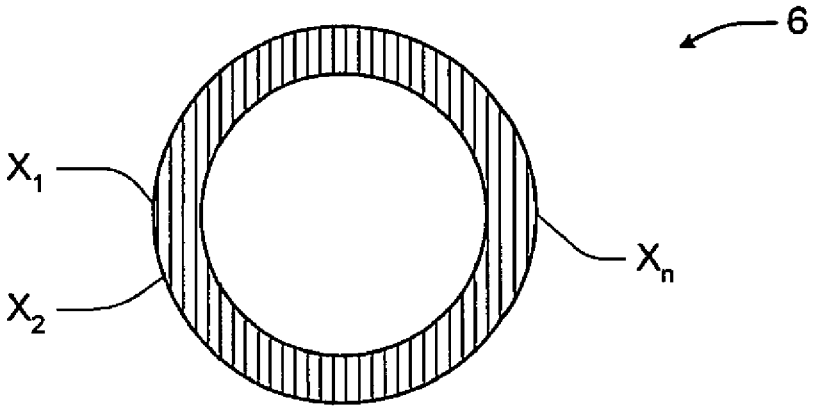
FIGS. 12-14 are schematic diagrams of variations on the embodiment of FIG. 11.
Figure 13:
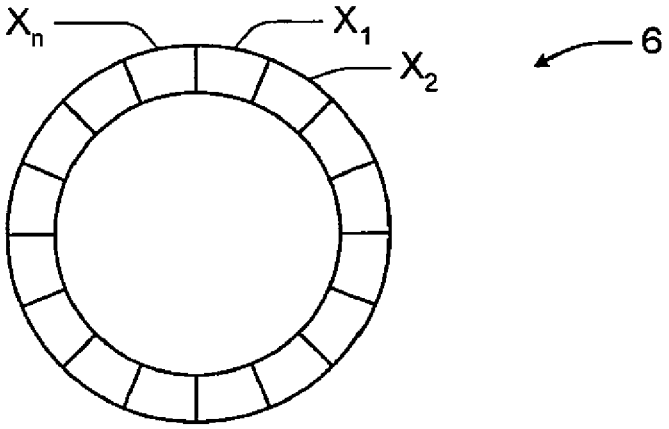
Figure 14:
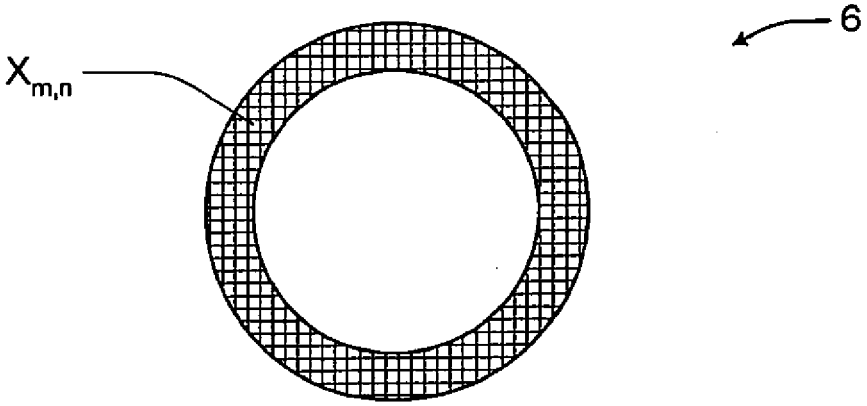

FIGS. 12-14 schematically illustrate possible patterns for individual transducing elements within annular transducer 6. FIG. 12 shows a collection of vertically striped individual elements denoted $X_1$ to $X_n$. FIG. 13 shows a collection of radially arranged sections. FIG. 14 shows a grid of sections denoted $X_{m,n}$ that could be activated individually or in groups according to any desired pattern (such as rows, columns, spokes, etc.). In each of these embodiments, individual transducing elements can be activated by ultrasonic generator 5 according to a time-based "rotation" or other pattern that enables three dimensional imaging techniques to be used by imager 9. Such "mini-tomographic" data may be gathered from two locations (two eyesockets) of the patent 4 and electronically combined by imager 9 to provide greater detail and thus accuracy of the diagnosis of stroke that would otherwise be available.

Of course, the use of multiple locations in the manner just described is not limited to only the transducer designs illustrated in FIGS. 10-14, but is an embodiment of the invention that can be practiced with any suitable transducer 6. For example, multiple transducers known as "EchoEye" by EchoCath, Inc. may be used to assemble a composite image by using the data generated by slight changes in the position, frequency and/or phase of the transducer, according to the principles taught in U.S. Pat. No. 5,373,845 (Gardineer et al.).

While the above description is in terms of diagnosis of stroke, it should be noted that any embodiment of the invention could be used in a two-step regimen in which the patient is first diagnosed with stroke, and then additional ultrasonic energy is delivered (perhaps at different frequency, power level and the like) during administration of a therapy such as tPA.

Some embodiments of the invention employ modified or unmodified aspects of otherwise known ultrasonic diagnostic systems. Such systems include those commercially available from, or under development by: Sonosite, Pie Medical, Esaote, the Bracco Group, Philips Medical Systems, ATL, Hewlett-Packard, Agilent Technologies, Toshiba, Toshiba Medical Systems, Toshiba America Medical Systems, General Electric, General Electric Medical Systems, EchoCath, Acuson, Endosonics, Aloka, Hitachi Siemens Medical Systems, Inc., 3D Echotech, Ecton, SPECS USA, Daum, and Multigon Industries.

Some embodiments of the invention employ modified or unmodified aspects of otherwise known non-ultrasonic diagnostic systems. Such systems include those commercially available from, or under development by: Non-Invasive Technology, Baylor College of Medicine; the Center for Innovative Minimally Invasive Therapy (CIMIT) of Massachusetts (including its member organizations such as Massachusetts General Hospital, Brigham and Women's Hospital, Draper Laboratory, and Massachusetts Institute of Technology); Harvard Medical School;

Such systems also include those disclosed in any of the documents listed below as incorporated by reference into this document.

Equipment

The invention may be implemented using standard or custom ultrasonic transducers, transmitters/receivers, image generation equipment, etc., by adapting such devices as appropriate to accomplish the objectives described above.

Suitable stabilization devices can be made by modifying existing cardiac tissue stabilizers, such as any of the inventions described and claimed in:

International Patent Application number PCT/NL94/00156 (International Publication Number WO 95/01757)
U.S. Pat. No. 5,865,730 (Fox et al.)
U.S. Pat. No. 5,984,864 (Fox et al.)
U.S. Pat. No. 5,894,843 (Benetti et al.)

Suitable vacuum-based stabilization devices can be made by modifying existing commercially available vacuum-based cardiac tissue stabilizers. Examples include the Medtronic Octopus®, Octopus2®, and Octopus®2+Tissue Stabilization Systems, or any similar product.

Suitable vacuum-based stabilization devices can be made by modifying known vacuum-based cardiac tissue stabilizers such as any of the inventions described or claimed in:

U.S. Pat. No. 5,836,311 (Borst et al.)
U.S. Pat. No. 5,927,284 (Borst et al.)
U.S. Pat. No. 6,015,378 (Borst et al.)
U.S. Pat. No. 5,727,569 (Benetti et al.)
U.S. Pat. No. 6,032,672 (Taylor)
U.S. Pat. No. 5,906,607 (Taylor et al.)
U.S. Pat. No. 5,782,746 (Wright)
U.S. Pat. No. 5,865,730 (Fox et al.)
U.S. Pat. No. 6,071,295 (Takahashi)
U.S. Pat. No. 6,007,523 (Mangosong)

U.S. Pat. No. 6,007,486 (Hunt et al.)
U.S. Pat. No. 5,891,017 (Swindle et al.)
U.S. Pat. No. 5,885,271 (Hamilton et al.)
U.S. Pat. No. 6,019,722 (Spence et al.)
International Patent Application Number PCT/US96/15091 (International Publication Number WO 97/10753)

Other suitable stabilization devices can be made by modifying existing vacuum-based eye tissue stabilizers such as Suction rings employed in Lasik™ brand laser surgery Devices disclosed in U.S. Pat. No. 5,171,245 (Sher)

Any known algorithms for detecting emboli or other aspects of blood flow can be used, including those described in the documents in the Appendix, and also:

U.S. Pat. No. 4,109,642 Reid et al.)
U.S. Pat. No. 5,042,490 (Federov et al.)
U.S. Pat. No. 5,348,015 (Moehring et al.)
International Patent Application Number PCT/US99/26740 (International Publication Number WO 00/27288)

The systems and methods employed in any known ultrasonic system may be adapted for use in embodiments of the invention. Such systems include those disclosed and claimed in the references in the Appendix, and especially the following:

U.S. Pat. No. 5,123,415 (Daigle)
U.S. Pat. No. 5,295,485 (Shinomura et al.)
U.S. Pat. No. 5,360,005 (Wilk)
U.S. Pat. No. 5,369,624 (Fukukita et al.)
U.S. Pat. No. 5,590,658 (Chiang et al.)
U.S. Pat. No. 5,690,114 (Chiang et al.)
U.S. Pat. No. 5,839,442 (Chiang et al.)
U.S. Pat. No. 5,904,652 (Gilbert et al.)
U.S. Pat. No. 5,957,846 (Chiang et al.)
U.S. Pat. No. 5,964,709 (Chiang et al.)
U.S. Pat. No. 6,106,472 (Chiang et al.)
U.S. Pat. No. 6,111,816 (Chiang et al.)
U.S. Pat. No. 5,709,209 (Friemel, et al.)
U.S. Pat. No. 5,722,412 (Pflugrath et al.)
U.S. Pat. No. 5,782,769 (Hwang et al.)
U.S. Pat. No. 5,817,024 (Ogle et al.)
U.S. Pat. No. 5,893,363 (Little, et al.)
U.S. Pat. No. 5,976,088 (Urbano et al.)
U.S. Pat. No. 6,004,270 (Urbana et al.)
U.S. Pat. No. 6,056,691 (Urbana et al.)
U.S. Pat. No. 6,086,537 (Urbana et al.)
U.S. Pat. No. 6,135,961 (Pflugrath et al.)
U.S. Pat. No. 6,126,608 (Kemme et al.)
U.S. Pat. No. 6,102,863 (Pflugrath et al.)
U.S. Pat. No. 6,106,468 (Dowdell)

Improvements

Based on this disclosure, there are several improvements to the invention that are clearly desirable and already understood by the inventors to be within the legal scope of the invention. In general, this includes any improvement, currently known or later discovered, in areas such as portable electronics, ultrasonic imaging systems, computer graphics, signal processing, stroke diagnosis and treatment, and the like, that is suitable for use with the invention.

Such improvements specially include those that do not depend for their function, operation, or success on the specific medical condition and diagnostic techniques this invention relies upon. In other words, improvements to any similar device that is not the invention could and should be applied to the invention, as appropriate.

Examples of improvements within the currently understood scope of the invention include:

Reduction in cost, weight, and power consumption.
Reduction in the time required to form an image.
Improvements in imaging quality
Reduction in time required to form an image.
Changes in shape, size, and format of the image.
Changes in shape, size, and format of the equipment.
Improved ergonomic design, such as improvement in the fit to the patient, ease of use by the operator, or any type of adaptation to a harsh or otherwise specialized operating environment.
Substitution of materials for any reason.
Improved reliability or quality.
Improved graphics, resolution, larger screen size.
Faster transfer and processing of data.
Remote transmission and/or processing of data.

Provided they lie within the scope of the claims below, or are considered equivalent under the law, the legal scope of the invention includes any improvements or changes of the types described above, even if they are developed after the date of this document.

DOCUMENTS INCORPORATED BY REFERENCE

The full disclosure of each of the following documents is incorporated into this document.

All books, articles, documents, publications, U.S. Patents, U.S. Patent Applications, and International Patent Applications cited elsewhere in this document.

The following medical textbooks:

Aaslid (ed.), Transcranial Doppler Sonography (1986), ISBN 3211819355
Babikian et al (eds.), Transcranial Doppler Ultrasound (2nd edition 1999) ISBN 0750699698
Barnett (ed.), Stroke (3rd edition, 1998), ISBN 0443075514
Bogdahn et al. (eds.), Echoenhancers and Transcranial Color Duplex Sonography (1998), ISBN 0632048565
Bogousslavsky (ed.), Stroke Syndromes (1995), ISBN 0521453976
Ebrahim and Harwood, Stroke (2nd edition, 1999), ISBN 0192628763
Greenberg (ed.), Neuroimaging: A Companion to Adams and Victor's Principles of Neurology (2nd edition, 1999), ISBN 0071346155
Hademos et al., The Physics of Cerebrovascular Diseases: Biophysical Mechanisms of Development, Diagnosis and Therapy (1998), ISBN 1563965585
Jensen and Jensen, Estimation of Blood Velocities Using Ultrasound: A Signal Processing Approach (1996), ISBN 0521464846
McGahan and Goldberg (eds.), Diagnostic Ultrasound (1998), ISBN 0397516142
Meyer, Diagnosis and Management of Stroke and TIAs (1982), ISBN 0201041847' Semple et al., An Atlas of Stroke (2nd edition 1999), ISBN 1850700826.
Millikan et al. (eds.), Stroke (1987), ISBN 0812110161
Newell and Aaslid, Transcranial Doppler (1991), ISBN 0881678368
Poeck, et al. (eds.), New Trends in Diagnosis and Management of Stroke (1987), ISBN 0387183698
Sandler et al., Correlative Imaging (1989), ISBN 0683075020
Tegeler et al., Neurosonology (1995), ISBN 0815187920
Tempkin, Ultrasound Scanning (2nd edition, 1998), ISBN 0721668798

Weinberger (ed.), Non-Invasive Imaging of Cerebrovascular Disease (1988) ISBN 08451-45045

Whisnant, Stroke (1993), ISBN 07506057X

Wiebers et al., Handbook of Stroke (1997), ISBN 0316947601.

The following engineering and medical literature:

Alexandrov et al., "The Evolving Role of Transcranial Doppler in Stoke Prevention and Treatment," Journal of Stroke and Cerebrovascular Diseases (March-April 1998)

Alexandrov et al., "Yield of Transcranial Doppler in Acute Cerebral Ischemia," Stroke (August 1999)

Alexandrov et al., "High Rate of Complete Recanalizatoin and Dramatic Clinical Recovery During tPA Infusion When Continuously Monitored With 2-MHz Transcranial Dopper Monitoring," Stroke (March 2000)

Baumgartner et al., "Contrast-Enhanced Transcranial Color-Coded Duplex Sonography in Ischemic Cerebrovascular Disease," Stroke (December 1997)

Boas et al., "Preliminary Investigation Into The Use Of Near Infrared Spectroscopy For Diagnosing And Monitoring Stroke," Proceedings of the SPIE Conference on Battlefield Biomedical Technologies (volume 3712, April 1999)

Boespflug, "Transcranial Doppler: First Results Of Exploration In The Circle Of Willis" [French, online abstract in English], Journal des Maladies Vascularies (1989)

Can et al., "Transcranial Doppler Ultrasound Criteria for Hemodynamically Significant Internal Carotid Artery Stenosis Based on Residual Lumen Diameter Calculated From En Bloc Endarterectomy Specimens," Stroke (October 1997)

Chen et al., "Biomechanics of Ocular Pneumoplethysmography," Journal of Biomechanical Engineering (August 1993)

Cheung et al., "Differentiation Between Intracerebral Hemorrhage and Ischemic Stroke by Transcranial Duplex Sonography: Response," Stroke (August 1999)

Cullinane et al., "Evaluation of New Online Automated Embolic Signal Detection Algorithm, Including Comparison With Panel of International Experts," Stroke (June 2000)

Cunningham et al., "Miniature Silicon Electronic Biological Assay Chip And Applications For Rapid Battlefield Diagnostics," Proceedings of the SPIE Conference on Battlefield Biomedical Technologies (volume 3712, April 1999)

Demchuk et al., "The Accuracy and Criteria for Localizing Arterial Occlusion with Transcranial Doppler," J. Neuroimaging (September 1999)

Dietrich et al., "Thromboembolic Events Predispose the Brain to Widespread Cerebral Infarction After Delayed Transient Global Ischemia in Rats," Stroke (April 1999)

Furni et al., "'Tail Sign' Associated With Microembolic Signals," Stroke (April 1999)

Kidwell et al., "Identifying Stroke in the Field: Prospective Validation of the Los Angeles Prehospital Stroke Screen (LAPSS)," Stroke (January 2000)

Gee, "Ocular Pneumoplethysmography," Survey of Ophthamology (January-February 1985)

Geissler, et al., "Cooling Gradients and Formation of Gaseous Microemboli With Cardiopulmonary Bypass: An Echographic Study," Annals of Thoracic Surgery (July 1997)

Giller et al., "Estimation of Vessel Flow and Diameter During Cerebral Vasospasm Using Transcranial Dopper Indices," Neurosurgery (May 1998)

Ginsberg et al. "Combating Hyperthermia in Acute Stroke," Stroke (February 1998)

Ginsberg et al., "Noninvasive Diagnosis Of Extracranial Cerebrovascular Disease: Oculoplethysmography-Phonoangiography And Directional Doppler Ultrasonography," Neurology (May 1979)

Grocott et al., "Cerebral Emboli and Serum S100β During Cardiac Operations," Annals of Thoracic Surgery (June 1998)

Gymnopoulos et al., "Low Pulsatility Signals Through the Orbits," Stroke (February 1996)

Hoskins et al., "A Flow Model Of Cerebral Aneurysms For Use With Power Doppler Studies," British Journal of Radiology (January 1998)

Hoskins, et al., "Colour Ultrasound Imaging Of Blood Flow And Tissue Motion," British Journal of Radiology (September 1997)

Ito et al., "A Comparison Of The Accuracy Of Cerebral Blood Flow Measurement Suing Transorbital Doppler Flow Velocity Vs. Transcranial Doppler Flow Velocity," Anesthesiology (September 1998, Supplement)

Kaposzta et al., "Clinical Application of Asymptomatic Embolic Signal Detection in Acute Stroke: A Prospective Study" Stroke (September 1999)

Kemény et al., "Automatic Embolus Detection by a Neural Network," Stroke (April 1999)

Klein et al., "Retinal Emboli and Stroke," Archives of Ophthalmology (August 1999)

Klötzsch et al., "Emboli Detection During Continuous-Wave Doppler Sonography of Internal Carotid Artery Stenosis," Journal of Stroke and Cerebrovascular Diseases (March-April 1998)

Kogan et al., "Model-Based Visualization Of Ultrasound Images," Proceedings of the SPIE Conference on Battlefield Biomedical Technologies (volume 3712, April 1999)

Krongold et al., "Quadratic Time-Scale Detection Of Microemboli In Flowing Blood With Doppler Ultrasound," Proceedings of SPIE Signal and Image Processing V (San Diego, Calif., 1997)

Krongold et al., "Time-Scale Detection of Microemboli in Flowing Blood with Doppler Ultrasound," IEEE Transactions on Biomedical Engineerin (September 1999)

Larkin, "Sounding Out The Brain With Transcranial Doppler," The Lancet (Feb. 28, 1998)

Leonhirth, "Near-IR Sensor Monitors Brain Lesions," Biophotonics International (July/August 1999)

Levine et al., "'Telestroke': The Application of Telemedicine for Stroke," Stroke (February 1999)

Ling, et al., "In Search Of Technological Solutions For Combat Casualty Care," Proceedings of the SPIE Conference on Battlefield Biomedical Technologies (volume 3712, April 1999)

Markus et al. "Microscopic Air Embolism During Cerebral Angiography And Strategies For Its Avoidance," The Lancet (Mar. 27, 1993)

Markus et al., "Improved Automated Detection of Embolic Signals Using a Novel Frequency Filtering Approach," Stroke (August 1999)

Martin et al., "Is The Continued Use Of Ocular Pneumoplethysmography Necessary For The Diagnosis Of Cerebrovascular Disease?" Journal of Vascular Surgery (February 1990)

Mäurer et al., "Differentiation Between Intracerebral Hemorrhage and Ischemic Stroke by Transcranial Color-Coded Duplex-Sonography," Stroke (December 1998)

McRae et al., "Pressure And Volume Measurements From The Eye For Detecting Possible Arterial Obstruction," Annals of Biomedical Engineering (January 1984)

Miller et al. "Ultrasound Contrast Agents Nucleate Inertial Cavitation In Vitro," Ultrasound in Medicine and Biology (August 1995)

National Institute of Neurological Disorders and Stroke, Proceedings of the National Symposium on Rapid Identification and Treatment of Acute Stroke, Dec. 12-13, 1996

Nicholas et al., "The Cerebral Hyperperfusion Syndrome: Diagnostic Value Of Ocular Pneumoplethysmography," Journal of Vascular Surgery (April 1993)

Nuzzaci et al., "Duplex Scanning Exploration of the Opthalmic Artery for the Detection of the Hemodynamically Significant ICA Stenosis," Stroke (April 1999)

Petitti, "The Hyperdense Middle Cerebral Artery Sign," Radiology (September 1998)

Polak et al. "Hypoechoic Plaque at US of the Carotid Artery: An Independent Risk Factor for Incident Stroke in Adults Aged 65 or Older," Radiology (September 1998)

Postert et al. "Contrast-Enhanced Transcranial Color-Coded Sonography in Acute Hemispheric Brain Infarction," Stroke (September 1999)

Riechers et al., "Hemorrhage Detection Using Electromagnetic Waves: Animal Test Results," Proceedings of the SPIE Conference on Battlefield Biomedical Technologies (volume 3712, April 1999)

Rorick, "Indications for Diagnostic Tests in the Evaluation of Stroke," Heart Disease and Stroke (November/December 1994)

Schmidt et al., "Noninvasive Prediction of Intracranial Pressure Curves Using Transcranial Doppler Ultrasonography and Blood Pressure Curves," Stroke (December 1997)

Schneider et al., "Noninvasive Assessment of Cerebral Collateral Blood Supply Through the Ophthalmic Artery," Stroke (January 1991)

Shaffer et al., "Virtual Rounds: Simulation-Based Education In Procedural Medicine," Proceedings of the SPIE Conference on Battlefield Biomedical Technologies (volume 3712, April 1999)

Soller et al., "Noninvasive NIR Measurement Of Tissue Ph To Assess Hemorrhagic Shock In Swine," Proceedings of the SPIE Conference on Battlefield Biomedical Technologies (volume 3712, April 1999)

Spencer et al. "Transorbital Doppler Diagnosis Of Intracranial Arterial Stenosis," Stroke (September 1986)

Steinke, "Power Doppler Imaging of Carotid Artery Stenosis," Stroke (October 1997)

Stolz et at, "Frontal Bone Windows for Transcranial Color-Coded Duplex Sonography," Stroke (April 1999)

Tong et al. "Incidence Of Transcranial Doppler-Detected Cerebral Microemboli In Patients Referred For Echocardiography," Stroke (November 1994)

Tong et al., "Transcranial Doppler-Detected Microemboli in Patients With Acute Stroke," Stroke (September 1995)

Valdueza et al., "Monitoring of Venous Hemodynamics in Patients With Cerebral Venous Thrombosis by Transcranial Doppler Ultrasound," Archives of Neurology (February 1999)

Vuadens et al., "Diagnosis as a Guide to Stroke Therapy," The Lancet (1998 volume 352 Supplement III).

Ward, "Seeing is Believing," ADVANCE for Administrators in Radiology and Radiation Oncology (January 1999)

Warlow, "Epidemiology of Stroke" The Lancet, (1998 volume 352 Supplement III)

Wolstenhuhne, et al., "The Agreement Between Colour Doppler Systems In Measuring Internal Carotid Artery Peak Systolic Velocities," British Journal of Radiology (October 1997).

The following U.S. Pat. Nos. 6,135,961; 6,111,816; 6,106,472; 6,086,537; 6,056,691; 6,004,270; 5,976,088; 5,975,081; 5,970,025; 5,967,991; 5,967,991; 5,964,709; 5,961,462; 5,957,846; 5,954,675; 5,954,053; 5,940,123; 5,938,607; 5,935,071; 5,924,988; 5,922,945; 5,921,928; 5,919,138; 5,919,137; 5,917,190; 5,916,168; 5,904,652; 5,903,516; 5,899,865; 5,897,851; 5,897,498; 5,893,363; 5,893,363; 5,891,035; 5,879,303; 5,879,303; 5,873,821; 5,860,924; 5,855,556; 5,853,370; 5,851,186; 5,839,442; 5,837,900; 5,833,613; 5,827,969; 5,820,558; 5,817,024; 5,817,024; 5,807,263; 5,800,356; 5,795,297; 5,792,051; 5,782,769; 5,782,769; 5,782,755; 5,779,631; 5,770,823; 5,770,801; 5,769,079; 5,768,939; 5,762,067; 5,752,517; 5,729,508; 5,722,412; 5,722,412; 5,720,710; 5,720,708; 5,720,291; 5,718,229; 5,715,823; 5,713,362; 5,713,362; 5,707,607; 5,707,606; 5,690,114; 5,673,701; 5,669,388; 5,669,388; 5,669,385; 5,664,574; 5,660,909; 5,655,539; 5,648,942; 5,647,364; 5,645,066; 5,640,960; 5,636,631; 5,635,619; 5,634,466; 5,634,465; 5,630,418; 5,617,863; 5,606,972; 5,603,323; 5,596,987; 5,595,723; 5,590,658; 5,582,176; 5,573,751; 5,568,384; 5,562,098; 5,558,855; 5,558,853; 5,558,094; 5,555,887; 5,553,614; 5,546,946; 5,540,230; 5,540,230; 5,529,070; 5,517,994; 5,494,038; 5,492,134; 5,492,121; 5,488,953; 5,485,842; 5,482,047; 5,482,045; 5,479,930; 5,476,097; 5,474,073; 5,471,990; 5,471,989; 5,456,257; 5,450,851; 5,438,994; 5,425,370; 5,425,370; 5,421,336; 5,409,688; 5,409,005; 5,402,793; 5,402,778; 5,390,675; 5,390,674; 5,386,827; 5,381,795; 5,373,845; 5,373,845; 5,373,845; 5,365,929; 5,353,799; 5,348,015; 5,343,865; 5,343,865; 5,343,865; 5,329,927; 5,329,927; 5,329,927; 5,305,756; 5,295,485; 5,295,307; 5,287,753; 5,255,682; 5,233,994; 5,226,422; 5,226,420; 5,215,094; 5,207,225; 5,197,477; 5,187,672; 5,167,230; 5,161,536; 5,158,088; 5,123,415; 5,122,974; 5,119,815; 5,103,827; 5,099,847; 5,095,910; 5,081,995; 5,076,278; 5,076,278; 5,062,428; 5,050,610; 5,016,641; 4,975,892; 4,975,723; 4,972,331; 4,926,871; 4,887,306; 4,883,059; 4,829,430; 4,817,618; 4,800,317; 4,691,418; 4,670,339; 4,658,827; 4,657,895; 4,644,795; 4,607,642; 4,603,702; 4,581,636; 4,567,895; 4,543,960; 4,542,653; 4,508,122; 4,508,122; 4,431,006; 4,430,898; 4,417,582; 4,411,360; 4,407,294; 4,399,704; 4,392,486; 4,354,502; 4,341,222; 4,298,009; 4,298,009; 4,282,880; 4,282,755; 4,282,577; 4,277,979; 4,258,576; 4,249,539; 4,237,902; 4,233,989; 4,222,274; 4,197,751; 4,197,749; 4,168,628; 4,165,182; 4,153,894; 4,131,024; 4,035,822; 4,019,818; 3,997,717; 3,978,508; 3,969,578; 3,953,822.

Alternative Embodiments

The following numbered aspects of the invention are part of the original disclosure of this invention. They are written as if they were individual inventions, so that they may be specifically considered as such in subsequent applications. Thus, some of the following may duplicate the claims at the end of this application. Some of them may contain additional limitations than those claims.

1. Diagnosing stroke using dynamic coupling of at least one ultrasonic transducer/receiver to a skull.
2. Using non-ultrasonic detection of symptoms of stroke to dynamically couple an ultrasonic transducer/receiver to a skull.
3. The method of invention 2 in which the non-ultrasonic detection comprises computed tomography scanning.
4. The method of invention 2 in which the non-ultrasonic detection comprises magnetic resonance scanning.
5. The method of invention 2 in which the non-ultrasonic detection comprises differential spectrophotometric methods or near-infrared detection of tissue characteristics.

6. The method of invention 2 in which the non-ultrasonic detection comprises detection or measurement of a biological material.
7. The method of invention 2 in which the non-ultrasonic detection comprises detection or measurement of a chemical.
8. The method of invention 2 in which the non-ultrasonic detection comprises detection or measurement of S100β.
9. The method of invention 2 in which the non-ultrasonic detection comprises use of biological assay techniques.
10. The method of invention 2 in which the non-ultrasonic detection comprises detection of change in blood pressure.
11. The method of invention 2 in which the non-ultrasonic detection comprises detection of change in pressure within the eye.
12. The method of invention 2 in which the non-ultrasonic detection comprises detection of change in blood flow in arteries serving organs other than the brain.
13. The method of invention 2 in which the non-ultrasonic detection comprises detection of change in blood flow in the arteries serving the eye.
14. For a patient having a skull containing brain tissue and blood vessels, and in a process for diagnosing stroke in the patient, a subprocess of dynamic coupling at least one ultrasonic transducer/receiver to at least one opening in the skull.
15. For a patient having a skull containing brain tissue and blood vessels, and in a process for diagnosing stroke in the patient, a subprocess of stabilizing at least one ultrasonic transducer/receiver to at least one opening in the skull.
16. For a patient having a skull containing brain tissue and blood vessels, and in a process for diagnosing stroke in the patient, a subprocess of compensating at least one ultrasonic transducer/receiver coupled to at least one opening in the skull.
17. For a patient having a skull containing brain tissue and blood vessels, and in a process for diagnosing stroke in the patient, a subprocess of compensating an image produced from at least one ultrasonic transducer/receiver coupled to at least one opening in the skull.
18. For a patient having a skull containing brain tissue and blood vessels, and in a process for diagnosing stroke in the patient, a subprocess comprising:
   a) dynamically coupling at least one of the ultrasonic transmitter/receivers to at least one opening in the skull of the patient; and
   b) imaging the brain tissue or blood vessels.
19. The subprocess of any of inventions 14 to 18, further comprising generating and receiving ultrasonic signals suitable for processing into information about the brain tissue or blood vessels.
20. The subprocess of any of inventions 14 to 18, further comprising applying a vacuum to the skull.
21. The subprocess of any of inventions 14 to 18, further comprising applying an acoustic coupling material to the skull.
22. The subprocess of any of inventions 14 to 18, in which the ultrasonic transducer/receiver is coupled to at least one man-made opening in the skull.
23. The subprocess of any of inventions 14 to 18, in which the ultrasonic transducer/receiver is coupled to at least ocular opening in the skull.
24. The subprocess of any of inventions 14 to 18, in which the ultrasonic transducer/receiver is coupled to at least one nasal opening in the skull.
25. The subprocess of any of inventions 14 to 18, in which the ultrasonic transducer/receiver is coupled to at least one aural opening in the skull.
26. The subprocess of any of inventions 14 to 18, in which the ultrasonic transducer/receiver is coupled to at least one acoustic bone window in the skull.
27. For a patient having a skull containing brain tissue and blood vessels, a process for diagnosing hemorrhagic stroke in the patient, comprising:
   a) dynamically coupling at least one ultrasonic transmitter/receiver to at least one opening in the skull of the patient;
   b) imaging a region within the skull of the patient; and
   c) determining presence of hemorrhagic stroke by identifying relatively diffuse blood flow within the skull of the patient.
28. The process of invention 27, in which the imaging comprises generating and receiving ultrasonic signals suitable for processing into information about the region within the skull of the patient.
29. The process of invention 27, in which a region is classified in terms of normal blood flow.
30. The process of invention 27, in which a region is classified in terms of inadequate blood flow.
31. The process of invention 27, in which a region is classified in terms of relatively diffuse blood flow.
32. The process of invention 27, in which locations of hemorrhagic stroke are determined by identifying relatively diffuse blood flow outside the blood vessels of the brain.
33. For a patient having a skull containing blood vessels, a process for diagnosing ischemic stroke in the patient, comprising:
   a) dynamically coupling at least one ultrasonic transmitter/receiver to at least one opening in the skull of the patient;
   b) imaging a region within the skull of the patient; and
   c) determining presence of ischemic stroke by identifying at least one location of inadequate blood flow within the skull of the patient.
34. The process of invention 33 in which the imaging comprises generating and receiving ultrasonic signals suitable for processing into information about the region within the skull of the patient.
35. The process of invention 33 in which a region is classified in terms of normal blood flow.
36. The process of invention 33 in which a region is classified in terms of inadequate blood flow.
37. The process of invention 33 in which a region is classified in terms of relatively diffuse blood flow.
38. The process of invention 33 in which locations of ischemic stroke are determined by identifying relatively inadequate blood flow within the blood vessels of the brain.
39. The process of invention 33 in which presence of ischemic stroke is determined by identifying at least one location where there is at least partial blockage of blood flow.
40. For a patient having a skull containing brain tissue and blood vessels, a process for diagnosing between hemorrhagic and ischemic stroke, comprising:
   a) dynamically coupling at least one ultrasonic transmitter/receiver to at least one opening in the skull of the patient;
   b) imaging a region within the skull of the patient; and
   c) classifying a region within the skull of the patient in terms of adequacy of blood flow.
41. The process of invention 40 in which the imaging comprises generating and receiving ultrasonic signals suitable for processing into information about the region within the skull of the patient.
42. The process of invention 40 in which a region is classified in terms of normal blood flow.

43. The process of invention 40 in which a region is classified in terms of inadequate blood flow.
44. The process of invention 40 in which a region is classified in terms of relatively diffuse blood flow.
45. The process of invention 40 in which locations of hemorrhagic stroke are determined by identifying relatively diffuse blood flow outside the blood vessels of the brain.
46. The process of invention 40 in which locations of ischemic stroke are determined by identifying relatively inadequate blood flow within the blood vessels of the brain.
47. The process of invention 40 in which presence of ischemic stroke is determined by identifying at least one location where there is at least partial blockage of blood flow.
48. The process of any of inventions 27, 33, or 40, further comprising applying a vacuum to the skull.
49. The process of any of inventions 27, 33, or 40, further comprising applying an acoustic coupling material to the skull.
50. The process of any of inventions 27, 33, or 40, in which the ultrasonic transducer/receiver is coupled to at least one man-made opening in the skull.
51. The process of any of inventions 27, 33, or 40, in which the ultrasonic transducer/receiver is coupled to at least ocular opening in the skull.
52. The process of any of inventions 27, 33, or 40, in which the ultrasonic transducer/receiver is coupled to at least one nasal opening in the skull.
53. The process of any of inventions 27, 33, or 40, in which the ultrasonic transducer/receiver is coupled to at least one aural opening in the skull.
54. The process of any of inventions 27, 33, or 40, in which the ultrasonic transducer/receiver is coupled to at least one acoustic bone window in the skull.
55. For a patient having a skull containing blood vessels serving a brain, a system for diagnosing hemorrhagic stroke in the patient, comprising:
   a) at least one ultrasonic transmitter/receiver receiver which generates and receives ultrasonic signals suitable for imaging the blood vessels of the brain,
   b) at least one apparatus to dynamically couple any of the ultrasonic transmitter/receivers to at least one opening in the skull of the patient; and
   c) a processor for imaging the blood vessels of the brain from at least one signal received from at least one ultrasonic transmitter/receiver.
56. For a patient having a skull containing blood vessels serving a brain, a system for diagnosing ischemic stroke in the patient, comprising.
   a) at least one ultrasonic transmitter/receiver receiver which generates and receives ultrasonic signals suitable for imaging the blood vessels of the brain,
   b) at least one apparatus to dynamically couple any of the ultrasonic transmitter/receivers to at least one opening in the skull of the patient; and
   c) a processor for imaging the blood vessels of the brain from at least one signal received from at least one ultrasonic transmitter/receiver.
57. For a patient having a skull containing blood vessels serving a brain, a system for discriminating between hemorrhagic stroke and ischemic stroke in the patient, comprising:
   a) at least one ultrasonic transmitter/receiver receiver which generates and receives ultrasonic signals suitable for imaging the blood of the brain,
   b) at least one apparatus to dynamically couple any of the ultrasonic transmitter/receivers to at least one opening in the skull of the patient; and
   c) a processor for imaging the blood vessels of the brain from at least one signal received from at least one ultrasonic transmitter/receiver.
58. The system of any of inventions 55, 56, or 57, further comprising acoustic coupling material positioned between the ultrasonic transmitter/receiver and the skull.
59. The system of any of inventions 55, 56, or 57, in which the ultrasonic transducer/receiver is coupled to at least one man-made opening in the skull.
60. The system of any of inventions 55, 56, or 57, in which the ultrasonic transducer/receiver is coupled to at least ocular opening in the skull.
61. The system of any of inventions 55, 56, or 57, in which the ultrasonic transducer/receiver is coupled to at least one nasal opening in the skull.
62. The system of any of inventions 55, 56, or 57, in which the ultrasonic transducer/receiver is coupled to at least one aural opening in the skull.
63. The system of any of inventions 55, 56, or 57, in which the ultrasonic transducer/receiver is coupled to at least one acoustic bone window in the skull.
64. The system of any of inventions 55, 56, or 57, in which more than one transducer/receiver is dynamically coupled to a like number of openings, but only a single image is produced.
65. An apparatus for diagnosing hemorrhagic stroke in a patient having a skull containing brain tissue and blood vessels, comprising:
   a) at least one ultrasonic transmitter/receiver; and
   b) a subassembly that dynamically couples at least one ultrasonic transmitter/receiver to the skull of the patient.
66. An apparatus for diagnosing ischemic stroke in a patient having a skull containing brain tissue and blood vessels, comprising:
   a) at least one ultrasonic transmitter/receiver; and
   b) at least one subassembly that dynamically couples at least one ultrasonic transmitter/receiver to the skull of the patient.
67. An apparatus for diagnosing between hemorrhagic and ischemic stroke in a patient having a skull containing brain tissue and blood vessels, comprising:
   a) at least one ultrasonic transmitter/receiver; and
   b) at least one subassembly that dynamically couples at least one ultrasonic transmitter/receiver to the skull of the patient.
68. The apparatus of any of inventions 65, 66, or 67, in which the subassembly stabilizes the transducer/receiver to the skull.
69. The apparatus of any of inventions 65, 66, or 67, further comprising acoustic coupling material between the ultrasonic transmitter/receiver and the skull.
70. The apparatus of any of inventions 65, 66, or 67, in which acoustic coupling material may be inserted into or removed from a location between the ultrasonic transmitter/receiver and the skull.
71. The apparatus of any of inventions 65, 66, or 67, in which acoustic coupling material is supported by a disposable member that may be inserted into or removed from a location between the ultrasonic transmitter/receiver and the skull.
72. The apparatus of any of inventions 65, 66, or 67, in which normal operation of the apparatus is prevented in the absence of an acoustic coupling material.
73. The apparatus of any of inventions 65, 66, or 67, in which normal operation of the apparatus occurs only in the presence of a sufficient amount of an acoustic coupling material.

74. The apparatus any of inventions 65, 66, or 67, in which the apparatus further comprises:
   a) a subapparatus that determines a quantity of an acoustic coupling material positioned between the ultrasonic transmitter/receiver and the skull, and
   b) a subapparatus that modifies normal operation of the apparatus based on the determined quantity of acoustic coupling material.
75. The apparatus of any of inventions 65, 66, or 67, in which the apparatus further comprises a subapparatus that inserts acoustic coupling material between the ultrasonic transmitter/receiver and the skull.
76. The apparatus of any of inventions 65, 66, or 67, in which the apparatus further comprises a subapparatus that receives acoustic coupling material between the ultrasonic transmitter/receiver and the skull.
77. The apparatus of any of inventions 65, 66, or 67, in which the apparatus inhibits diagnosis in the absence of sufficient acoustic coupling material.
78. The apparatus of any of inventions 65, 66, or 67, in which the apparatus permits diagnosis only in the presence of sufficient acoustic coupling material.
79. The apparatus any of inventions 65, 66, or 67, in which the apparatus further comprises:
   a) a subapparatus that determines a quantity of acoustic coupling material present and
   b) a subapparatus that modifies diagnosis based on the quantity of acoustic coupling material present.
80. The apparatus of invention 65, in which the apparatus further comprises:
   a) a subapparatus that determines a quantity of acoustic coupling material present and
   b) a subapparatus that bases the determination of hemorrhagic stroke, in part, on the quantity of acoustic coupling material present.
81. The apparatus of invention 66, in which the apparatus further comprises:
   a) a subapparatus that determines a quantity of acoustic coupling material present and
   b) a subapparatus that bases the determination of ischemic stroke, in part, on the quantity of acoustic coupling material present.
82. The apparatus of invention 67, in which the apparatus further comprises:
   a) a subapparatus that determines a quantity of acoustic coupling material present and
   b) a subapparatus that bases the discrimination between hemorrhagic stroke and ischemic stroke, in part, on the quantity of acoustic coupling material present.
83. A process, subprocess, apparatus, or system that detects or measures or assesses the amount or quality of dynamic coupling between a transducer/receiver and a skull, and then inhibits or permits or modifies diagnosis of stroke accordingly.
84. A process, subprocess, apparatus, or system that detects or measures or assesses the amount or quality of dynamic coupling between a transducer/receiver and a skull, and then inhibits or permits or modifies diagnosis of stroke accordingly using closed loop control of the amount or quality of dynamic coupling.
85. Each of the embodiments of invention 84 in which the closed loop control is performed using an algorithm selected from the group consisting essentially of all possible combinations of proportional control, integral control, and derivative control.
86. Each of the embodiments of invention 84 in which the amount or quality of dynamic coupling is adjusted by adjusting the extent of a vacuum applied to the skull.
87. Each of the embodiments of invention 84 in which the amount or quality of dynamic coupling is adjusted by adjusting the amount or location of an acoustic coupling material between the transducer/receiver and the skull.
88. Each of the embodiments of inventions 86 or 87 in which the amount or quality of dynamic coupling is adjusted in a single location.
89. Each of the embodiments of inventions 86 or 87 in which the amount or quality of dynamic coupling is adjusted in multiple locations by respective amounts that may or may not be the same in each location.
90. Each of the embodiments of invention 84 in which the amount or quality of dynamic coupling is adjusted by modifying an imaging process.
91. A process, subprocess, apparatus, or system for identifying type of stroke in a patient having a skull containing brain tissue and blood vessels, comprising:
   a) at least one ultrasonic transmitter/receiver; and
   b) at least one apparatus to dynamically couple at least one ultrasonic transmitter/receiver to the skull of the patient;

in which the process, subprocess, apparatus, or system:
   c) creates a non-Doppler ultrasonic image of a blood vessel serving the brain;
   d) creates a Doppler ultrasonic image of microparticulates flowing in the blood vessel; and
   e) identifies type of stroke based on flow rate of the microparticulates.
92. A process, subprocess, apparatus, or system for identifying type of stroke in a patient having a skull containing brain tissue and blood vessels, comprising.
   a) at least one ultrasonic transmitter/receiver; and
   b) at least one apparatus to dynamically couple at least one ultrasonic transmitter/receiver to the skull of the patient;

in which the process, subprocess, apparatus, or system:
   c) creates a harmonic ultrasonic image of the blood vessels serving the brain,
   d) creates a Doppler ultrasonic image of microparticulates flowing in the blood vessels serving the brain, and
   e) identifies type of stroke based on identification and comparison of at least one zone of diffuse blood flow and at least one zone of normal tissue.
93. A process, subprocess, apparatus, or system for dynamically coupling an ultrasonic transmitter/receiver to a skull of a patient such that the process, subprocess, apparatus, or system creates an ultrasonic image of brain tissue or blood vessels, comprising:
   a) positioning, adjacent the skull, a platform which comprises at least one suction port;
   b) coupling the platform to the patient by the application of suction to at least one suction port; and
   c) coupling the ultrasonic transmitter/receiver to the platform.
94. Each of embodiments of invention 93 in which the platform is shaped in at least a portion of a circular arc.
95. Each of embodiments of invention 93 in which the platform comprises at least two portions, each of which is shaped in at least a portion of a circular arc, the two portions being arranged generally opposite each other.
96. Each of embodiments of invention 93, further comprising adjusting the amount and/or location of acoustic coupling material between the ultrasonic transducer/receiver and the skull.

97. Any of the previous embodiments of inventions 1-96, embodied in a portable form suitable for mounting on the patient's head.
98. Any of the previous embodiments of inventions 1-97, in which the ultrasonic system is a portable system as disclosed (and especially as claimed) in any of the patents cited above that are assigned to Sonosite or ATL.
99. Any of the previous embodiments of inventions 1-97, in which the ultrasonic system uses techniques disclosed (and especially as claimed) in any of the patents cited above that are assigned to EchoCath, especially EchoFlow.
100. Any of the previous embodiments of inventions 1-99, in which the image processor includes an expert system.
101. Any of the previous embodiments of inventions 1-100, in which the image processor includes a neural network.

We claim:

[1. Using non-ultrasonic detection of symptoms of stroke to dynamically couple an ultrasonic transducer/receiver to a skull, in which the non-ultrasonic detection comprises at least one of the group consisting of computed tomography scanning, magnetic resonance scanning, differential spectrophotometric methods, near-infrared detection of tissue characteristics, detection of a biological material, measurement of a biological material, detection of a chemical, measurement of a chemical, detection of S100β, measurement of S100β, use of biological assay techniques, detection of change in blood pressure, detection of change in pressure within the eye, detection of change in blood flow in arteries serving organs other than the brain, or detection of change in blood flow in the arteries serving the eye.]

[2. For a patient having a skull containing brain tissue and blood vessels, a process for diagnosing stroke in the patient, comprising:

a) dynamically coupling at least one ultrasonic transmitter/receiver to at least one man-made opening in the skull of the patient;
b) imaging a region within the skull of the patient; and
c) at least one of: determining presence of hemorrhagic stroke by identifying relatively diffuse blood flow within the skull of the patient; determining presence of ischemic stroke by identifying at least one location of inadequate blood flow within the skull of the patient; and diagnosing between hemorrhagic and ischemic stroke by classifying a region within the skull of the patient in terms of adequacy of blood flow.]

[3. The process of claim 2, in which the imaging comprises generating and receiving ultrasonic signals suitable for processing into information about the region within the skull of the patient.]

[4. The process of claim 2, in which a region is classified in terms of normal blood flow.]

[5. The process of claim 2, in which a region is classified in terms of inadequate blood flow.]

[6. The process of claim 2, in which a region is classified in terms of relatively diffuse blood flow.]

[7. The process of claim 2, in which locations of hemorrhagic stroke are determined by identifying relatively diffuse blood flow outside the blood vessels of the brain.]

[8. The process of claim 2 in which locations of ischemic stroke are determined by identifying relatively inadequate blood flow within the blood vessels of the brain.]

[9. The process of claim 2 in which presence of ischemic stroke is determined by identifying at least one location where there is at least partial blockage of blood flow.]

[10. The process of claim 2, further comprising applying a vacuum to the skull.]

[11. The process of claim 2, further comprising applying an acoustic coupling material to the skull.]

*12. A combined portable automatic external defibrillator (AED) and stroke therapy device for the treatment of patients, the device comprising:*

*an automatic external defibrillator which gathers electrocardiogram (ECG) data;*

*an ultrasonic transducer, coupled to the automatic external defibrillator, which is adapted to be acoustically coupled to the brain of a subject to send and receive ultrasound signals;*

*imaging components configured to diagnose stroke from the ultrasound signals received by the ultrasound transducer and the ECG data;*

*a common power supply which powers both the automatic external defibrillator and the ultrasonic transducer; and*

*common audio or visual prompting equipment which prompts a user for proper use of the device,*

*wherein the ultrasonic transducer is configured to deliver additional ultrasonic energy during administration of a therapy following the diagnosis of stroke.*

*13. The combined portable AED and stroke therapy device of claim 12, wherein the common power supply includes a battery.*

*14. The combined portable AED and stroke therapy device of claim 12, wherein the automatic external defibrillator includes a defibrillator electrode.*

*15. The combined portable AED and stroke therapy device of claim 12, wherein the ultrasound transducer is an annular transducer.*

*16. The combined portable AED and stroke therapy device of claim 12, being further configured to diagnose a type of stroke.*

*17. The combined portable AED and stroke therapy device of claim 16, wherein the type of stroke includes an ischemic stroke.*

*18. The combined portable AED and stroke therapy device of claim 16, wherein the type of stroke includes a hemorrhagic stroke.*

*19. A combined portable automatic external defibrillator (AED) and stroke therapy device for the treatment of patients, the device comprising:*

*an automatic external defibrillator which gathers electrocardiogram (ECG) data;*

*an ultrasonic transducer, coupled to the automatic external defibrillator, which is adapted to be acoustically coupled to the brain of a subject to send and receive ultrasound signals; and*

*imaging components configured to diagnose stroke from the ultrasound signals received by the ultrasound transducer and the ECG data,*

*wherein the ultrasonic transducer is configured to deliver additional ultrasonic energy during administration of a therapy following the diagnosis of stroke.*

*20. The combined portable AED and stroke therapy device of claim 19, further comprising a common power supply which powers both the automatic external defibrillator and the ultrasonic transducer.*

*21. The combined portable AED and stroke therapy device of claim 19, further comprising common audio or visual prompting equipment which prompts a user for proper use of the device.*

*22. The combined portable AED and stroke therapy device of claim 20, wherein the common power supply includes a battery.*

*23. The combined portable AED and stroke therapy device of claim 19, wherein the automatic external defibrillator includes a defibrillator electrode.*

*24. The combined portable AED and stroke therapy device of claim 19, wherein the ultrasound transducer is an annular transducer.*

*25. The combined portable AED and stroke therapy device of claim 19, being further configured to diagnose a type of stroke.*

*26. The combined portable AED and stroke therapy device of claim 19, wherein the type of stroke includes an ischemic stroke.*

*27. The combined portable AED and stroke therapy device of claim 19, wherein the type of stroke includes a hemorrhagic stroke.*

* * * * *